(12) United States Patent
Zwierstra et al.

(10) Patent No.: US 11,540,967 B2
(45) Date of Patent: *Jan. 3, 2023

(54) HEADSET SYSTEM

(71) Applicant: NovaSignal Corp., Los Angeles, CA (US)

(72) Inventors: Jan B. Zwierstra, Los Angeles, CA (US); Trevor Dunlop, Los Angeles, CA (US); Lane Stith, Los Angeles, CA (US); Gerard Salinas, Los Angeles, CA (US)

(73) Assignee: NovaSignal Corp., Los Angeles, CA (US)

( * ) Notice: Subject to any disclaimer, the term of this patent is extended or adjusted under 35 U.S.C. 154(b) by 392 days.

This patent is subject to a terminal disclaimer.

(21) Appl. No.: 16/281,938

(22) Filed: Feb. 21, 2019

(65) Prior Publication Data

US 2019/0175433 A1 Jun. 13, 2019

Related U.S. Application Data

(63) Continuation of application No. 15/853,433, filed on Dec. 22, 2017, now Pat. No. 10,272,008.

(Continued)

(51) Int. Cl.
*A61G 13/12* (2006.01)
*A61B 8/08* (2006.01)
(Continued)

(52) U.S. Cl.
CPC .......... *A61G 13/121* (2013.01); *A61B 5/0075* (2013.01); *A61B 5/055* (2013.01);
(Continued)

(58) Field of Classification Search
CPC ...... A61G 13/121; A61B 5/055; A61B 5/702; A61B 8/0808; A61B 5/0075;
(Continued)

(56) References Cited

U.S. PATENT DOCUMENTS

| 5,265,625 A | 11/1993 | Bodman |
| 6,778,849 B1 * | 8/2004 | Ninomiya ............... A61B 5/055 |
| | | 324/318 |

(Continued)

FOREIGN PATENT DOCUMENTS

| JP | 2000-116645 A | 4/2000 |
| JP | 2007-508853 A | 4/2007 |
| WO | WO-2015/075603 A1 | 5/2015 |

OTHER PUBLICATIONS

International Preliminary Report on Patentability dated Sep. 19, 2019, from application No. PCT/US2017/068336.

(Continued)

*Primary Examiner* — Sanjay Cattungal
(74) *Attorney, Agent, or Firm* — Foley & Lardner LLP

(57) ABSTRACT

Arrangements described herein relate to a headset system and a method to manufacturing the headset system, the headset system including a headset configured to lay on top of a surface and to support a head of a subject when the subject is in a supine position or a reclined position, at least one probe adjustment mechanism, and a probe coupled to the at least one probe adjustment mechanism and configured to emit acoustic energy.

17 Claims, 19 Drawing Sheets

Related U.S. Application Data

(60) Provisional application No. 62/467,782, filed on Mar. 6, 2017.

(51) Int. Cl.
*A61B 8/00* (2006.01)
*A61B 5/00* (2006.01)
*A61B 5/11* (2006.01)
*A61B 5/055* (2006.01)
*A61B 6/03* (2006.01)
*A61B 6/04* (2006.01)

(52) U.S. Cl.
CPC .......... *A61B 5/1127* (2013.01); *A61B 5/6814* (2013.01); *A61B 5/702* (2013.01); *A61B 8/0808* (2013.01); *A61B 8/40* (2013.01); *A61B 8/4218* (2013.01); *A61B 8/488* (2013.01); *A61B 6/032* (2013.01); *A61B 6/0428* (2013.01); *A61B 6/0442* (2013.01); *A61B 6/0492* (2013.01); *A61B 8/4272* (2013.01); *A61B 8/4405* (2013.01); *A61B 8/4416* (2013.01); *A61B 8/4477* (2013.01); *A61B 2562/12* (2013.01)

(58) Field of Classification Search
CPC ..... A61B 5/1127; A61B 5/6814; A61B 8/488; A61B 8/40; A61B 8/4218; A61B 6/032; A61B 6/0428; A61B 6/0442; A61B 6/0492; A61B 8/4272; A61B 8/4405; A61B 8/4416; A61B 8/4477; A61B 2562/12
See application file for complete search history.

(56) References Cited

U.S. PATENT DOCUMENTS

| | | | | |
|---|---|---|---|---|
| 9,526,440 | B2* | 12/2016 | Burnside | A61B 90/40 |
| 2009/0093685 | A1* | 4/2009 | Vu | A61G 13/12 |
| | | | | 600/300 |
| 2011/0251489 | A1* | 10/2011 | Zhang | A61B 8/4227 |
| | | | | 600/459 |
| 2013/0035585 | A1* | 2/2013 | Martens | A61B 5/055 |
| | | | | 600/411 |
| 2015/0265216 | A1* | 9/2015 | Andrews | A61B 18/04 |
| | | | | 128/845 |
| 2015/0297176 | A1* | 10/2015 | Rincker | A61B 8/429 |
| | | | | 600/439 |
| 2015/0297303 | A1 | 10/2015 | Heindl et al. | |
| 2016/0015588 | A1* | 1/2016 | Tamiya | A61G 15/125 |
| | | | | 128/845 |
| 2016/0030001 | A1* | 2/2016 | Stein | A61B 5/0095 |
| | | | | 600/431 |
| 2016/0278736 | A1* | 9/2016 | Hamilton | A61B 8/4227 |
| 2016/0317129 | A1* | 11/2016 | Seip | A61B 8/483 |
| 2017/0119347 | A1* | 5/2017 | Flores, II | A61B 8/488 |
| 2017/0188992 | A1* | 7/2017 | O'Brien | G16H 50/30 |
| 2017/0188993 | A1* | 7/2017 | Hamilton | A61B 8/0808 |
| 2017/0188994 | A1* | 7/2017 | Flores, II | A61B 8/4444 |
| 2018/0021021 | A1* | 1/2018 | Zwierstra | A61B 8/10 |
| | | | | 600/453 |
| 2018/0049762 | A1* | 2/2018 | Seip | A61B 8/0891 |
| 2018/0169443 | A1* | 6/2018 | Wurster | A61B 90/10 |

OTHER PUBLICATIONS

International Search Report and Written Opinion dated Apr. 23, 2018, from application No. PCT/US2017/068336.
U.S. Final Office Action dated Sep. 25, 2018, from U.S. Appl. No. 15/853,433.
U.S. Non-final Office Action dated Mar. 9, 2018, from U.S. Appl. No. 15/853,433.
U.S. Notice of Allowance dated Dec. 19, 2018, from U.S. Appl. No. 15/853,433.
Extended European Search Report dated Oct. 16, 2020, from application No. 17900120.1.

* cited by examiner

HEADSET SYSTEM

CROSS-REFERENCE TO RELATED PATENT APPLICATIONS

This application is a continuation of U.S. application Ser. No. 15/853,433, filed Dec. 22, 2017, which claims the benefit of and priority to U.S. provisional patent application Ser. No. 62/467,782, filed Mar. 6, 2017, the contents of each of which are incorporated herein by reference in their entireties.

BACKGROUND

For devices utilizing a headset for which performance is optimized by remaining stable with respect to a user's head (e.g., optical devices, virtual reality headsets, surgical devices, ultrasound devices, imaging devices, automated Transcranial Doppler devices, and so on), many are designed to have the subject sit vertically during operation. With respect to medical devices that are headsets (e.g., devices for monitoring neurological activity), after many head traumas or in response to neurological conditions, a patient may often not be able to sit or stand and may be laying down, or may even be unconscious (e.g., during an emergency situation). Accordingly, headsets designed for subjects sitting or standing vertically may not sit or operate correctly. Furthermore, traditional robotic or manual headset devices designed to be worn by the subject may weigh several pounds and therefore strain the neck muscles or head structure of the subject.

SUMMARY

Various embodiments relate to systems and methods for providing a headset, which allows a patient's head to be held while also providing a mount for a manual or robotic headset such that the headset can operate while the patient is laying down (e.g., in a supine position) or reclined. Accordingly, the weight of the headset system is substantially or completely supported by the surface upon which the headset is placed, rather than supported by the subject. In addition, according to various embodiments, the headset does not need to be secured to the subject's head, but rather to the surface upon which the headset rests, resulting in greater comfort and less anxiety for the subject.

In some arrangements, a headset system includes a headset configured to lay on top of a surface and to support a head of a subject when the subject is in a supine position or a reclined position, at least one probe adjustment mechanism, and a probe coupled to the at least one probe adjustment mechanism and configured to emit acoustic energy.

In some arrangements, the headset includes a head cradle configured to receive and retain the head of the subject.

In some arrangements, the headset includes a baseplate extending laterally from the headset, and the at least one probe adjustment mechanism and the probe are contained within a robotic pod supported by the baseplate.

In some arrangements, the robotic pod extends substantially perpendicular from the baseplate.

In some arrangements, the headset and the robotic pod are configured to be entirely supported by the surface.

In some arrangements, the baseplate has a plurality of slots at different locations along a length of the baseplate, each of the plurality of slots configured to retain the robotic pod such that a location of the robotic pod is adjustable along the baseplate.

In some arrangements, the head cradle includes a plurality of side restraints opposite to each other and configured to restrict lateral movement of the head of the subject.

In some arrangements, each of the plurality of side restraints has a leading edge having a ramped surface configured to allow the headset to slide underneath the head of the subject when the subject is in the supine position or the reclined position.

In some arrangements, the head cradle includes a center restraint configured to contact the forehead of the subject.

In some arrangements, the center restraint is configured to pivot about a hinge to adjustably engage and disengage a forehead of the subject.

In some arrangements, the headset is made from non-metal materials and is configured to be positioned in an imaging tool.

In some arrangements, the imaging tool includes a magnetic resonance imaging (MRI) scanner or computed tomography (CT) scanner.

In some arrangements, the headset system further includes at least one strap attached to the headset, wherein the at least one strap is configured to anchor the headset system to the surface.

In some arrangements, the surface is defined by a bed or a gurney.

In some arrangements, the headset is configured to contact a back of the head and a back of a neck of the subject.

In some arrangements, the probe is located proximate or in contact with a temporal window of the head of the subject.

In some arrangements, the probe includes an ultrasound probe configured to emit ultrasound energy.

In some arrangements, the at least one probe adjustment mechanism includes robotics for automatically controlling positioning of the probe against a temporal window of the subject.

In some arrangements, the probe adjustment mechanism includes a manual mechanism for manually controlling positioning of the probe against a temporal window of the subject.

In some arrangements, a method of manufacturing a headset system, the method includes providing a headset configured to lay on top of a surface and to support a head of a subject when the subject is in a supine position or a reclined position, providing at least one probe adjustment mechanism, and coupling a probe to the at least one probe adjustment mechanism, the probe configured to emit acoustic energy.

BRIEF DESCRIPTION OF THE FIGURES

Features and aspects will become apparent from the following description and the accompanying example embodiments shown in the drawings, which are briefly described below.

DETAILED DESCRIPTION

Figure 1:
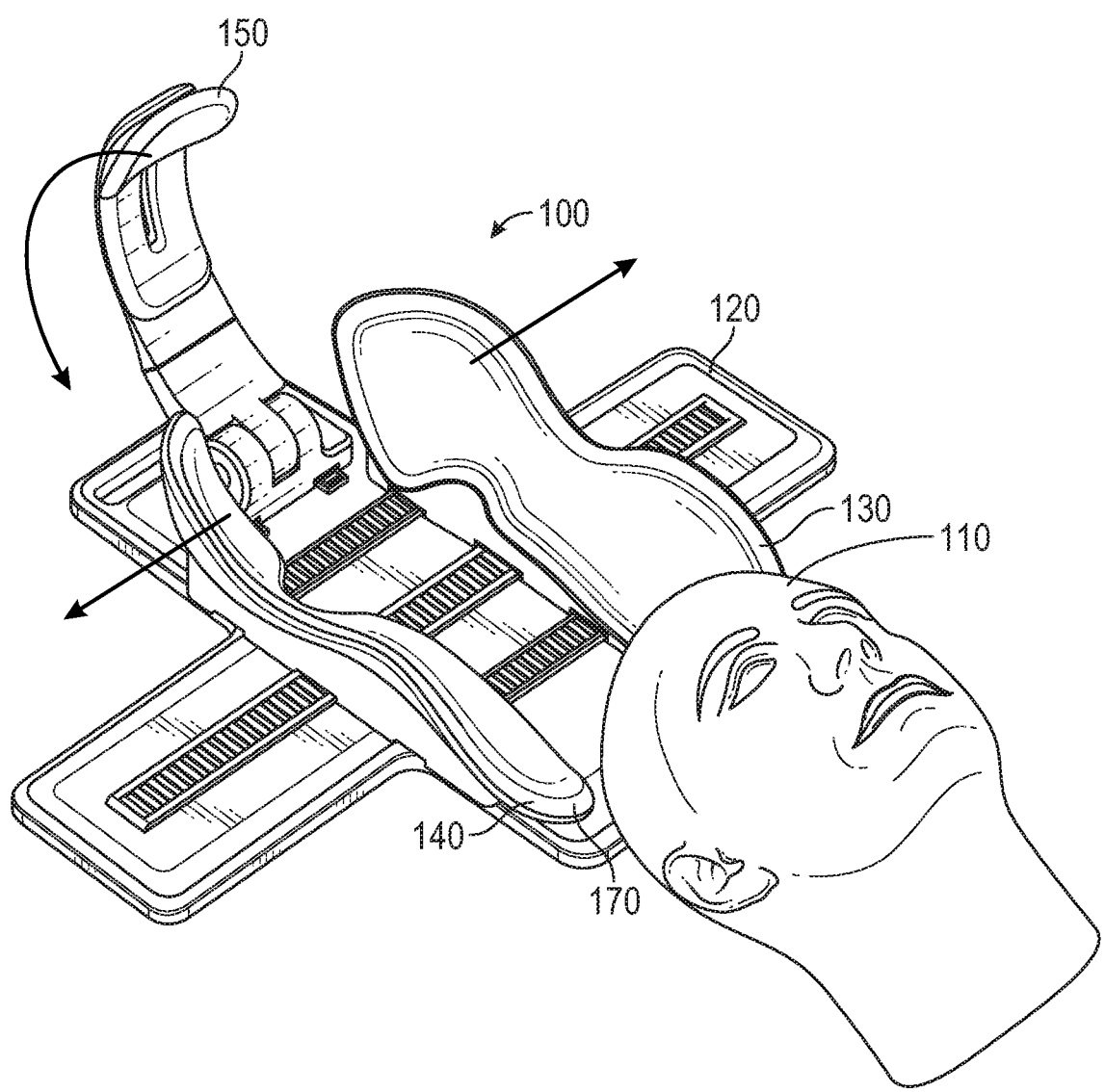
FIG. 1 illustrates a perspective view of a headset according to various embodiments.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements that may be practiced. It is to be understood that other arrangements may be utilized, and structural changes may be made without departing from the scope of the various arrangements disclosed in the present disclosure.

After many head traumas or in response to neurological conditions (e.g., stroke), a patient may often not be able to sit or stand and may be laying down, or may even be unconscious (e.g., during an emergency situation). For example, stroke patients may typically be aphasic or agitated. Accordingly, in some arrangements, a headset including a platform (e.g., a baseplate) allows a patient to lay down while the headset is operational (e.g., in the supine or reclined position). Furthermore, in some arrangements, a supine headset restrains a patient's head while increasing the patient's comfortability (e.g., such that the headset minimizes claustrophobic sensations). Comparing to the traditional headsets designed to be worn by the patient when the patient is standing or sitting, some arrangements described herein reduce the stress and strain on the patient's body, particularly in the head and neck region, by allowing the patient to lay down when the headset is being operated such that the headset is substantially supported by a surface on which the headset rests. In addition, according to some arrangements, headsets do not include a strap or restraint that goes around the head (e.g., around a portion of the or the entire circumference of the head) for anchoring a device (e.g., a TCD device) thereto, as the strap or restraint can be uncomfortable and/or induce anxiety for a patient. Accordingly, patient experience with respect to arrangements of the headsets as disclosed herein can be drastically improved.

In addition, arrangements described herein further promote accuracy with respect to aligning the patient to the headset. Given that the head (e.g., the temporal window region) may be the focus for testing by the headset, a headset designed to be worn by the patient when the patient is either standing or sitting can be difficult to align to the patient's head because only the feet or the backside of the patient is grounded, leaving the rest of the patient's body prone to swaying or other movement. Even when such a headset has been initially aligned, the headset is likely to become misaligned during the operation because some parts of the patient's body, such as, but not limited to, the torso, the neck, and the waist naturally sway or otherwise move, and do not remain perfectly still. The misalignment can be further exacerbated by the discomfort (e.g., the stress to the patient's body) of the conventional headsets due to the fact that such discomfort irritates the patient, causing him or her to move. On the other hand, the arrangements disclosed herein allow the patient to wear the headset while the patient is lying on a substantially flat surface (e.g., a bed, a gurney, and the like), such that all parts of the patient's body are on an immobile surface and/or on the platform/baseplate of the system. Accordingly, swaying or other movement of the patient's body is reduced or eliminated, or the movement of the patient has a reduced effect on the headset itself (e.g., because the patient's body does not support the headset). As further disclosed herein, the platform/baseplate can also have support structures structurally configured to hold the patient's body in place while the patient is laying on the surface. The precision of the tests can therefore be improved.

Some arrangements disclosed herein relate to a system that combines one or more robotic pods (e.g., ultrasound pods) with a headset configured to lay on a surface while supporting a head of a patient who is in a supine or reclined position. In some arrangements, at least a part (e.g., a connecting portion that connects the rest of the robotic pods with the headset) of the robotic pods and the headset are made from a unitary structure or material. In other arrangements, at least a part (e.g., the connecting portion) of the robotic pods is operatively coupled to the headset (e.g., a baseplate) via screws, clamps, Velcro®, hinges, joints, slots, clips, buckles, or other suitable fastening mechanisms. The headset or the baseplate may be detachable from the rest of the system (e.g., from the robotic pods) in some arrangements.

Given the baseplate's flat shape, the device and/or the baseplate itself can be easily stored, transported, assembled, and disassembled. As the baseplate may provide the structural support of the patient's head and the rest of the system for operation, a care provider can easily set up the test due to the lightweight, flat nature of the baseplate. For example, an operator can simply lay a subject's head into the arrangements described herein and begin operation of the system, as opposed to conventional designs in which an operator fits, secures, adjusts, and aligns a headset to a patient, which can be difficult to accomplish and result in longer time frames of health care administration and frustration to the operator and the patient.

Accordingly, arrangements described herein allow the system to be operated in various places or under various circumstances that were previously unimaginable. For example, a headset including a platform/baseplate can be placed in a magnetic resonance imaging (MRI) scanner so that the patient need not be moved from the platform/baseplate. For example, the platform/baseplate and a head cradle configured to receive the patient's head can be made from a plastic or other non-metal material that does not interfere with the MRI scanner operation, and the manual or robotic pods (e.g., which may contain materials that interfere with the MRI scanner operation) that are coupled to the platform/baseplate can be removed therefrom so that the patient can easily be transported to the MRI scanner without movement of the patient's head from the platform/baseplate. In some arrangements, a headset allows a view of the patient's face so that testing can be administered while the patient is on the platform, such as a National Institutes of Health Stroke Scale (NIHSS) test.

FIG. 1 illustrates a perspective view of a headset (e.g., a supine headset or headset configured to be used on a patient in a reclined position) 100 according to various arrangements. In some arrangements, the supine headset 100 provides a passive restraint for the head 110 of a patient that physically and physiologically allows minimal movement of the head 110. In some arrangements, the supine headset 100 includes a baseplate 120, as well as a left-side restraint 130 and a right-side restraint 140 attached to the baseplate 120. The baseplate 120 is designed to lay flat on a bed (e.g., gurney) or flat ground so that the patient may lie in a horizontal or reclined position. In some arrangements, a center restraint 150 is also included. When a patient lies with his or her head 110 on the baseplate 120, and the left-side restraint 130 and the right-side restraint 140 are in place, the patient's head 110 will be stabilized and restrained from twisting or lateral movements. The supine headset 100 provides a passive head restraint or cradle that opens up and allows the platform to be slid under the patient for limiting movement of the head 110 or neck.

In some arrangements, the maximum thickness of the baseplate 120 in the area slid under the patient is in a range from approximately ⅝ inches to approximately ¾ inches so that it can easily be slid under but also limits lifting of the head 110 when the subject is positioned. The material of the baseplate 120 can be rigid, such as, but not limited to, acrylonitrile butadiene styrene (ABS), nylon, steel, aluminum, composite, and the like or can be semi-flexible, such as, but not limited to, rubber. In some arrangements, the width of the baseplate 120 is no larger than about 24 inches so as to be compatible with a standard gurney width. In some arrangements, the entire supine headset 100 is designed to be easily sterilized by, for example, bleaching, autoclaving, boiling, or other suitable sterilizing technique. In some arrangements, the supine headset 100 is foldable for space-saving considerations. In some arrangements, the supine headset 100 (e.g., as shown in FIG. 1) does not include metal so that it can be placed in a computed tomography (CT) or MRI scanner without removal (e.g., so that the patient can be transferred in the passive restraint from the time emergency medical services are provided all the way through the imaging process).

In some arrangements, some or all of the supine headset 100 (e.g., the baseplate 120) is made from any suitable rigid material, such as, but not limited to, hard plastic, metals, aluminum, steel, titanium, magnesium, various alloys, rigid plastics, composites, carbon fiber, fiber glass, expanded foam, compression molded foam, stereolithography (SLA) or Fused Deposition Modeling (FDM)-made materials, Reaction Injection Molding (RIM) molding, acrylonitrile butadiene styrene (ABS), thermoplastic olefin (TPO), nylon, polyvinyl chloride (PVC), fiber reinforced resins, or the like.

The supine headset 100 allows for quick mounting, release and adjustment of medical devices such as Transcranial Doppler (TCD) robots at the left-side restraint 130 and the right-side restraint 140. In some arrangements, the supine headset 100 is attached to gurneys, chairs or hospital beds using attachment features such as, but not limited to, anchor holes, a series of slots, mechanical clips, side release buckles, or any other suitable fastening mechanism. In some arrangements, the supine headset 100 is designed to accommodate the use of a cervical collar or any other immobilization device.

In some arrangements, the left-side restraint 130, the right-side restraint 140 and the baseplate 120 define a head cradle upon which the head 110 of the subject rests. The head cradle is configured to receive, retain, and restrain the head 110. In some arrangements, the head cradle is configured to retain the back of the head 110 and the back of the neck of the subject for added comfort and stability. In addition, in some arrangements, the head cradle promotes stability by not only providing a seating area that limits head roll due to its shape, but can also clamp the head 110. For example, the left-side restraint 130 and the right-side restraint 140 exert an inward force towards the center of the baseplate 120 such that the head 110 is clamped between the left-side restraint 130 and the right-side restraint 140. In some arrangements, the clamping force of the left-side restraint 130 and the right-side restraint 140 is configured to be strong enough to retain the head 110 therebetween, but gentle enough to maintain comfort of the subject.

Accordingly, in some arrangements, the supine headset 100 is configured to retain and support the head 110 of the subject while the supine headset 100 is being supported by the surface on which the supine headset 100 rests, rather than being supported by the subject. Such configurations confer various characteristics, including, but not limited to, further comfort and stability to the subject and ease of use by an operator of the supine headset 100. In other words, in some arrangements, the weight of the supine headset 100 is supported (e.g., partially, substantially, or completely) by the surface on which the supine headset 100 rests. In some examples, the supine headset 100 and at least one manual or robotic pod are configured to be at least partially or entirely supported by the surface.

In some arrangements, the side restraints 130, 140 include padding for providing comfort to the head 110. In some arrangements, the padding is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like. In some arrangements, the padding of the side restraints 130, 140 has any suitable firmness for supporting the head 110, such as, but not limited to, in a range of about 0.1 pound per square inch (psi) to about 60 psi (e.g., in a range of about 0.1 psi to about 10 psi) or within other suitable ranges of firmness.

In some arrangements, the padding of the side restraints 130, 140 has memory for expanding to fit contours of the head 110. In some arrangements, the padding (e.g., foam) of the side restraints 130, 140 is compressed and expands after the head 110 is placed in the supine headset 100 so that the padding expands to secure the headset 100. In some arrangements, the side restraints 130, 140 including the padding is manufactured by any suitable process for affixing the padding within the headset 100, such as, but not limited to, injection molding, laminating, adhesive mounting (e.g., gluing or bonding), co-molding, co-casting, injection, snapping, by Velcro fastening, by hook and loop fastening, friction fitting, attaching with barbs, using screw bosses, or the like.

In other arrangements, the padding of the side restraints 130, 140 includes an inflatable bladder. In some arrangements, the bladder is a hollow void that is filled manually or with a pump. In such arrangements, the inflatable bladder is self-inflating with an internal structure that has a memory and that expands within the bladder to inflate to at least 90% capacity. In further arrangements, inflation is assisted with an integrated pump or an external filling or pumping source. In some arrangements, the inflatable bladder is filled with air, gas, liquid, or any other suitable element for affixing or securing the inflatable padding of the headset 100 to the subject's head 110. In other arrangements, the bladder is filled with plastic beads or pellets. In particular arrangements, the bladder that is filled with plastic beads or pellets becomes rigid, so as to capture the patient's head 110, when a vacuum is applied to the bladder.

Figure 2:
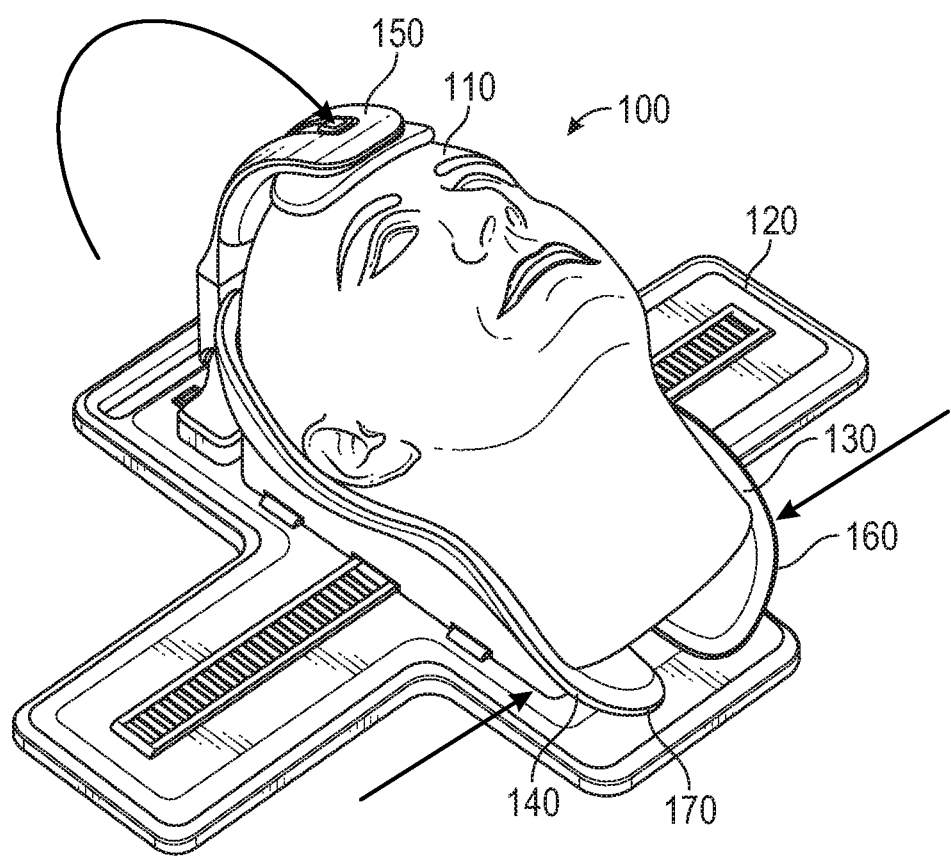
FIG. 2 illustrates a perspective view of a headset encasing a patient's head according to various embodiments.

FIG. 2 illustrates a perspective view of the supine headset 100 encasing the patient's head 110 according to various arrangements. Referring to FIG. 2, in some arrangements, the supine headset 100 is slid under the head 110 of the patient. The center restraint 150, left-side restraint 130, and right-side restraint 140 are secured around the head 110 to render the head 110 relatively immobile such that the patient's head 110 remains sufficiently restrained. In some arrangements, a left-side leading edge 160 of the left-side restraint 130 and a right-side leading edge 170 of the right-side restraint 140 are made of a semi-flexible or polished rigid surface. In some arrangements, the left-side leading edge 160 and the right-side leading edge 170 are designed to be slid under the head 110 of a patient and are a maximum of approximately 0.1 inches thick to create a ramped surface to aid in sliding the supine headset 100 under the head 110 when the subject is in the supine or the reclined position.

In some arrangements, the center restraint 150 is configured to pivot about a hinge so as to toggle between restraining/engaging the head 110 and disengaging/separating from the forehead. In some arrangements, the head 110 is laid within the head cradle and the center restraint 150 is secured to the forehead of the head 110 to make firm contact therewith. In some arrangements, the center restraint 150 includes a padding that makes contact with the head 110, and the padding is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like.

Figure 3:
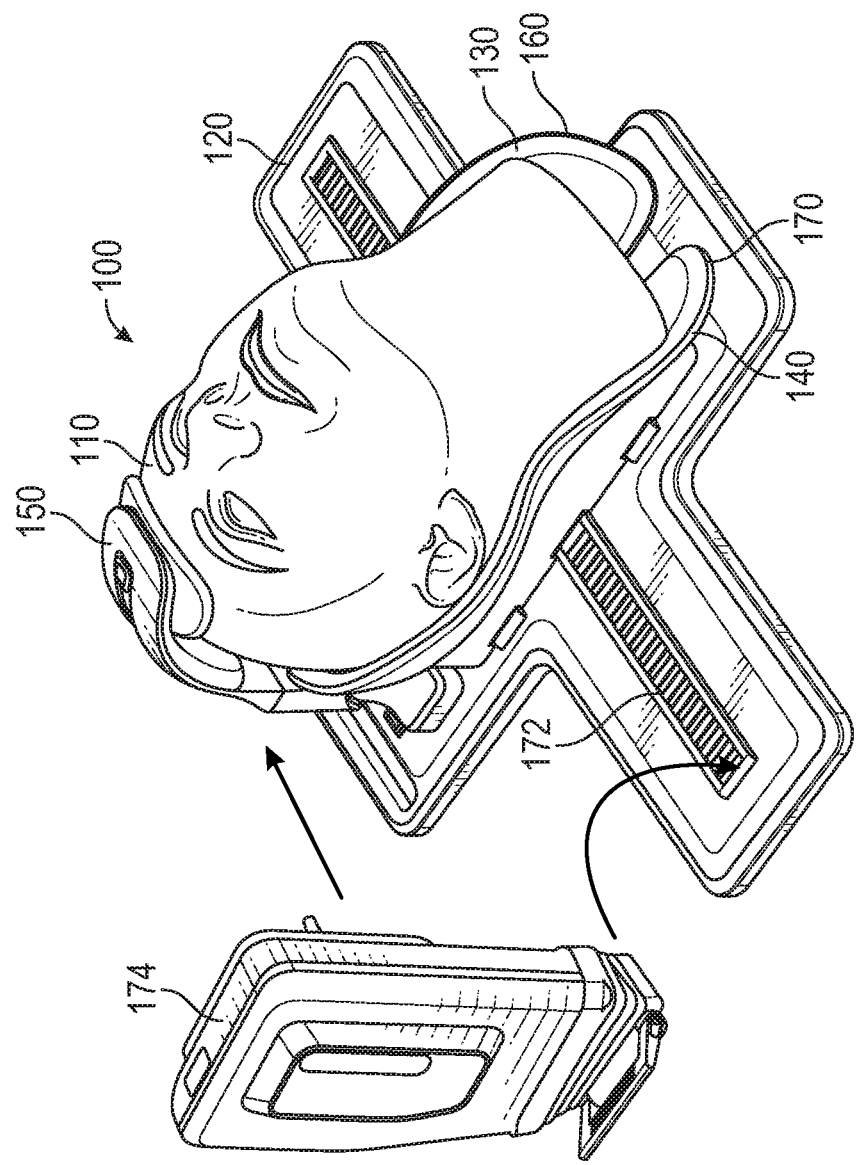
FIG. 3 illustrates a perspective view of a headset encasing a patient's head and a robotic pod according to various embodiments.

FIG. 3 illustrates a perspective view of the supine headset 100 encasing the patient's head 110 and a robotic pod 174 according to various arrangements. Referring to FIG. 3, in some arrangements, the supine headset 100 includes the baseplate 120 having a plurality of slots 172 into which the robotic pod 174 (e.g., a robotic pod including an ultrasound device, such as, but not limited to, a TCD device) can be placed. In some arrangements, the robotic pod 174 is secured or fastened to the railway of slots 172 and slid along the railway such that the robotic pod 174 is proximate the head 110. In some arrangements, the robotic pod 174 is adjustably locked along the railway. For example, the robotic pod 174 can latch onto any given one of the slots 172 to lock into place, thereby providing adjustability of the robotic pod 174 with respect to the distance from the head 110, and thereby allowing the supine headset 100 to accommodate different sizes and shapes of subject heads. In some arrangements, the plurality of slots 172 are located along a lengthwise dimension of the baseplate 120, where the lengthwise dimension is greater than a widthwise dimension of the baseplate 120.

In some arrangements, the robotic pod 174 extends upwards from the baseplate 120. For example, the baseplate 120 extends outward and substantially perpendicular (e.g., in a first direction) from the length of the head cradle or head 110 of the subject (e.g., extending in a second direction), and the robotic pod 174 extends substantially perpendicular from the baseplate 120 (e.g., in a third direction). The baseplate 120 extends laterally from the head cradle or head 110. In some arrangements, the first direction, the second direction, and the third direction are different directions or axes from each other. In some arrangements, because the robotic pod 174 is attached on top of the baseplate 120 of the supine headset 100, the weight of the robotic pod 174 is also substantially or completely supported by the surface on which the supine headset 100 is placed, rather than being supported by the subject.

In some arrangements, the robotic pod 174 includes a device, such as, but not limited to, an ultrasound device (e.g., a TCD device). The device (e.g., ultrasound device) includes a probe (e.g., ultrasound probe) and robotics (e.g., a probe adjustment mechanism) for controlling the probe. In some arrangements, the device and probe are configured to emit energy waves (e.g., acoustic energy), such as, but not limited to, ultrasound, infrared, near-infrared spectroscopy (NIRS), x-rays, and the like. In other arrangements, the probe includes other devices that are translated along the patient's head 110, such as, but not limited to, a camera.

In some arrangements, the robotics are configured to translate the probe along a surface of the head 110 and to move the probe towards and away from the head 110. In some arrangements, an end of the probe interfaces with the robotics, and the robotics include components, such as, but not limited to, a motor assembly and the like for controlling the probe (e.g., control z-axis pressure, normal alignment, or the like of the probe).

In some arrangements, the probe includes a first end and a second end that is opposite to the first end. In some arrangements, the first end includes a concave surface that is configured to be adjacent to or contact a scanning surface (e.g., the head 110 of a subject). The concave surface is configured with a particular pitch to focus generated energy towards the scanning surface. In some arrangements, the ultrasound device is configured such that the first end of the probe is configured to be adjacent to or contact and align along the head 110 (e.g., a side of the human head 110), and the first end of the probe is configured to provide ultrasound wave emissions from the first end and directed into the human head (e.g., towards the brain). In other arrangements, the probe is configured to emit other types of waves during operation, such as, but not limited to, infrared, NIRS, x-rays, or the like.

In some arrangements, the second end of the probe is coupled to the robotics. In some arrangements, the second end of the probe includes a threaded section along a portion of the body of the probe, and the second end is configured to be secured in the robotics via the threads (e.g., by being screwed into the robotics). In other arrangements, the probe is secured in the robotics by any other suitable connecting means, such as, but not limited to, welding, adhesive, one or more hooks and latches, one or more separate screws, press fittings, or the like.

In other arrangements, the probe is attached within the headset 100 without any robotics (e.g., a robotic pod 174), such that the probe is configured to be manually operated by an operator while the headset 100 is positioned on the user's head 110. For example, the user's head 110 can be placed in the headset 100 and an operator can manually shift and orient the probe while the probe is activated. In other words, the probe adjustment mechanism of the headset 100 that controls the probe can be a manual probe adjustment mechanism. For example, instead of a robotic pod 174, the headset 100 can include a manual probe adjustment mechanism that is interacted with by an operator for orientation and movement of the probe.

Further disclosure regarding ultrasound and TCD devices that can be used in conjunction with the headsets described herein can be found in non-provisional patent application Ser. No. 15/399,735, entitled SYSTEMS AND METHODS FOR DETECTING NEUROLOGICAL CONDITIONS, and filed on Jan. 5, 2017, which is incorporated herein by reference in its entirety.

In some arrangements, the robotic pod 174 is modular and can be attached and detached from the supine headset 100. In some arrangements, the supine headset 100 is used in conjunction with a medical device for use with respect to a subject's head 110 (e.g., an ocular monitoring system, a breathing device, a device for monitoring neurological activity, a surgical device, an ultrasound device, an imaging device, a device for monitoring radioactive traces, or any other device that is optimized when the device itself is not positionally disturbed with respect to a user's head). In other arrangements, the supine headset 100 is used in conjunction with a non-medical device for use with respect to the subject's head 110 (e.g., a virtual reality eyepiece).

In some arrangements, the supine headset 100 (and other headsets described herein) holds other medical and non-medical devices (or robotic pods) that are used and stabilized with respect to the head 110. For example, in some arrangements, an ocular device is a device that is optimized by maintaining positioning and alignment with a subject's eyes (e.g., if the ocular device is shifted with respect to a subject's eyes, performance of the ocular device may decline). In some arrangements, the ocular device is attached at the headset apparatus 100 so as to cover the eyes of a patient. As an example of a non-medical device use, in some arrangements, the supine headset 100 can be used in connection with the ocular device that is a virtual reality device configured to provide a virtual experience to the subject.

In some arrangements, the ocular device is a medical device designed to track ocular behavior of a subject (e.g., to diagnose whether the user has experienced a concussion). In other arrangements, the ocular device is an ocular diagnosis or treatment tool for determining or adjusting vision of the user. As an example, the ocular device is a device for correcting imperfect vision of a user (e.g., laser eye surgery). As another example, in some arrangements, the ocular device is an ocular diagnostic tool for determining a vision prescription of a user, presence of one or more eye conditions (e.g., glaucoma, cataracts, ocular hypertension, uveitis, or the like), and so on. In some arrangements, the ocular device is designed to cover and interact with both eyes simultaneously or in sequence. In other arrangements, the ocular device is designed to cover and interact with a single eye (e.g., while the other eye remains uncovered). The ocular device can be provided with any of the headset apparatuses described herein.

In some arrangements, the patient's head 110 is allowed to move slightly while restrained within the headset 100, to increase comfortability of the patient. In particular arrangements, in the event that the head 110 shifts with respect to the robotic pod 174, the robotic pod 174 can sense as such (e.g., by sensing an abrupt change in the signal as the robotic pod 174 remains stable, indicating a movement of the head 110) and can cause the probe to shift or orient accordingly along with the patient's head 110. As such, in some embodiments, the robotic pod 174 tracks and automatically maintains alignment with the patient's head 110.

Figure 4:
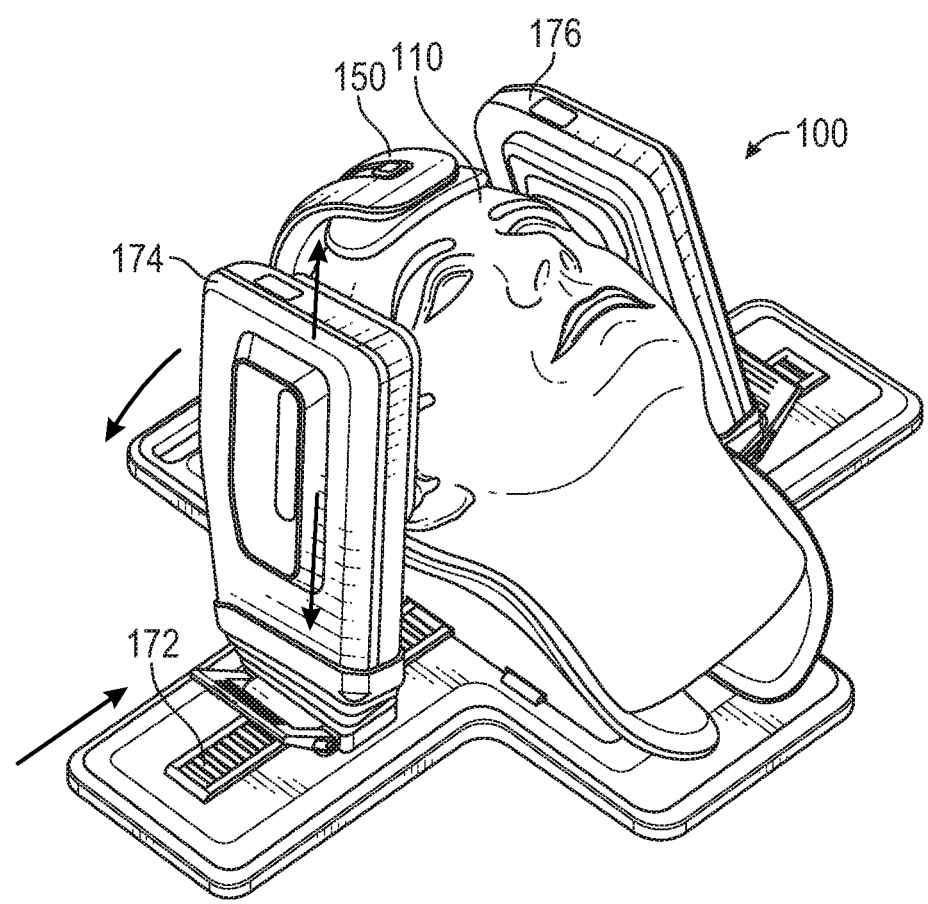
FIG. 4 illustrates a perspective view of a headset encasing a patient's head and including a plurality of robotic pods according to various embodiments.

FIG. 4 illustrates a perspective view of the supine headset 100 encasing a patient's head and including the plurality of robotic pods 174, 176 according to various arrangements. Referring to FIG. 4, in some arrangements, the supine headset 100 includes the robotic pods 174, 176 (e.g., including at least one ultrasound device, such as, but not limited to, TCD scanners) located at opposite sides of the supine headset 100. In some arrangements, the first robotic pod 174 and the second robotic pod 176 are placed in slots 172 on the baseplate 120 to allow both sides of the head 110 of the patient to be scanned simultaneously. In some arrangements, the head cradle (e.g., which includes the side restraints 130, 140), and therefore the head 110, is interposed between the first robotic pod 174 and the second robotic pod 176. As discussed above, positions of each of the robotic pods 174, 176 are adjustable along the railway of slots 172.

Figure 5:
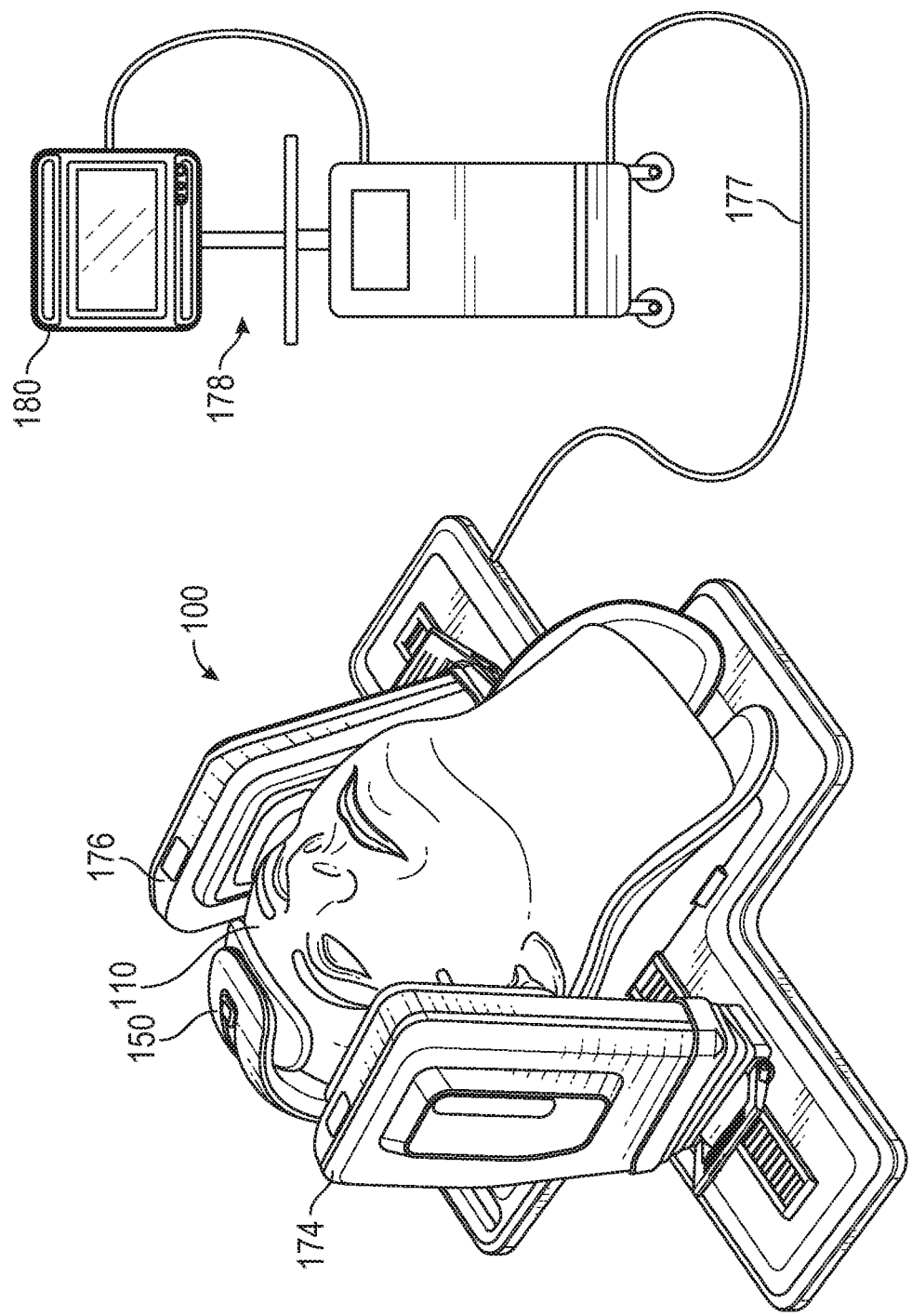
FIG. 5 illustrates a perspective view of a headset connected to a portable workstation according to various embodiments.

FIG. 5 illustrates a perspective view of the supine headset 100 connected to a portable workstation 178 according to various arrangements. Referring to FIG. 5, in some arrangements, the supine headset 100 (e.g., the robotic pods 174, 176) is connected via a cable 177 to the portable workstation 178 that includes a monitor 180 to display the results of scans of the head 110 of the patient. In other arrangements, the portable workstation 178 communicates with the robotic pods 174, 176 using wireless communication technologies such as, but not limited to, Bluetooth, Wi-Fi, or any other suitable wireless communication technology. In some arrangements, the system is modular so that different types of accessories other than robotic pods 174, 176 are attachable to the supine headset 100 (e.g., for use with respect to different applications of the supine headset 100, as described above).

Figure 6A:
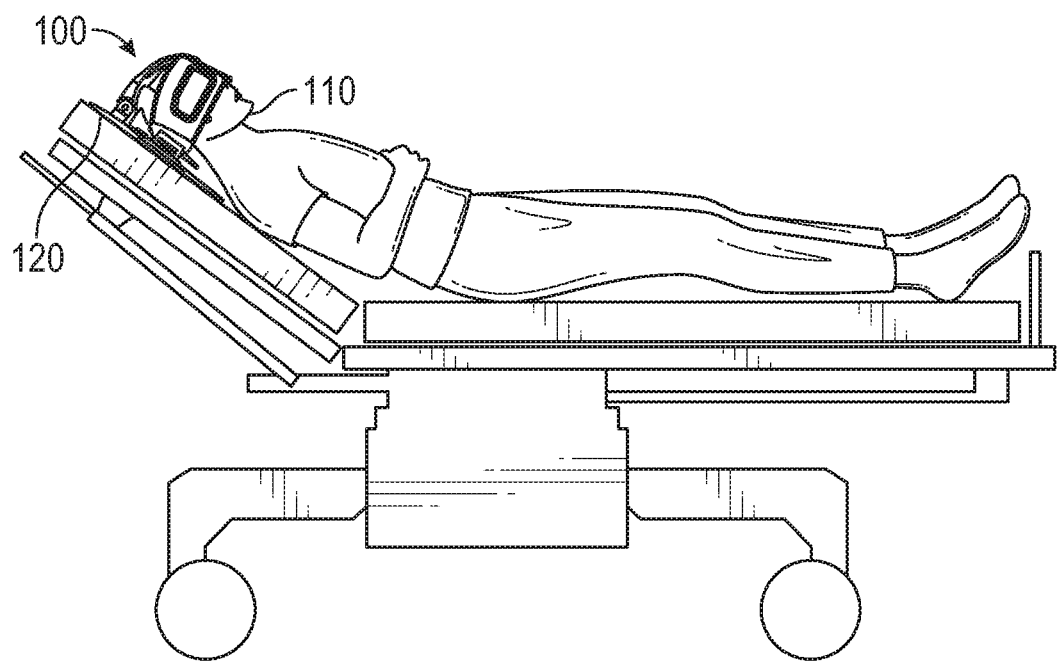
FIG. 6A illustrates an elevation view of a headset encasing a patient's head in a reclined position according to various embodiments.
Figure 6B:
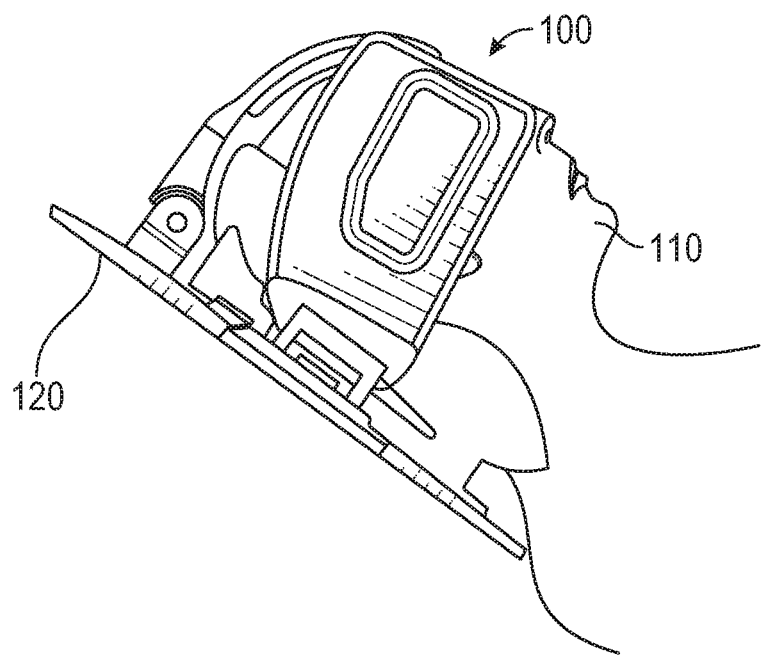
FIG. 6B illustrates an enlarged view of the headset encasing the patient's head as shown in FIG. 6A according to various embodiments.
Figure 6C:
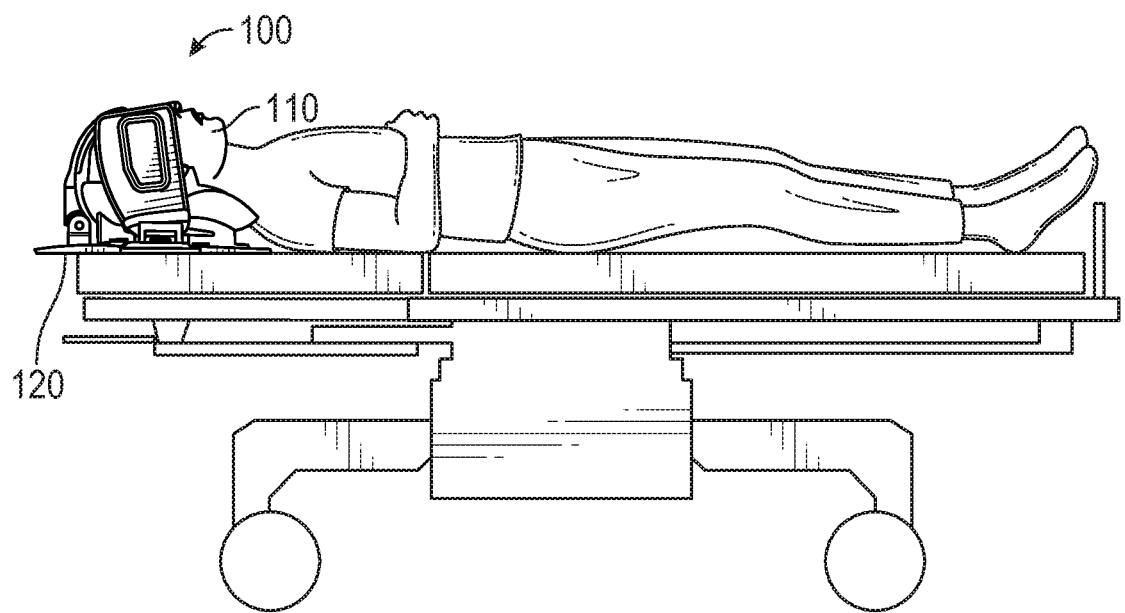
FIG. 6C illustrates an elevation view of a headset encasing a patient's head in a horizontal position according to various embodiments.
Figure 6D:
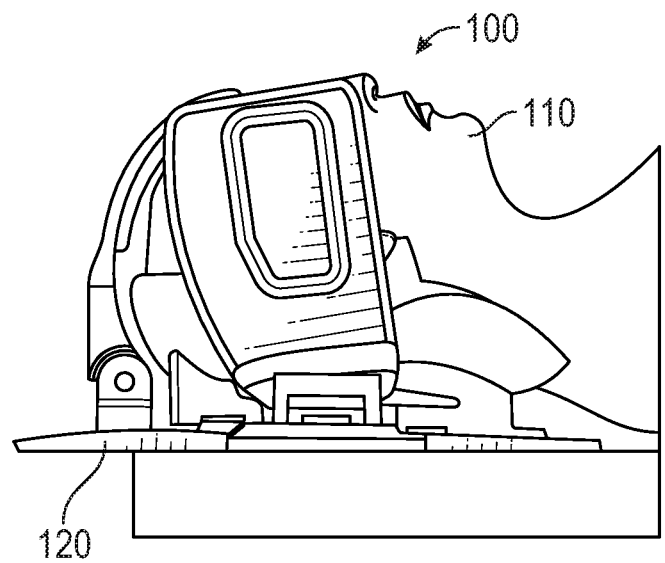
FIG. 6D illustrates an enlarged view of the headset encasing the patient's head as shown in FIG. 6C according to various embodiments.

FIG. 6A illustrates an elevation view of the supine headset 100 encasing the patient's head 110 in a reclined position according to various arrangements. FIG. 6B illustrates an enlarged view of the supine headset 100 encasing the patient's head 110 as shown in FIG. 6A according to various arrangements. FIG. 6C illustrates an elevation view of the supine headset 100 encasing the patient's head 110 in a horizontal position according to various arrangements. FIG. 6D illustrates an enlarged view of the supine headset 100 encasing the patient's head 110 as shown in FIG. 6C according to various arrangements. Referring to FIG. 6A, in some arrangements, the supine headset 100 is placed on the head 110 of the patient that is in a reclined position, as shown in further detail in FIG. 6B. Referring to FIG. 6C, in some arrangements, the supine headset 100 is placed on the head 110 of the patient that is in a horizontal position, as shown in further detail in FIG. 6D.

Figure 7A:
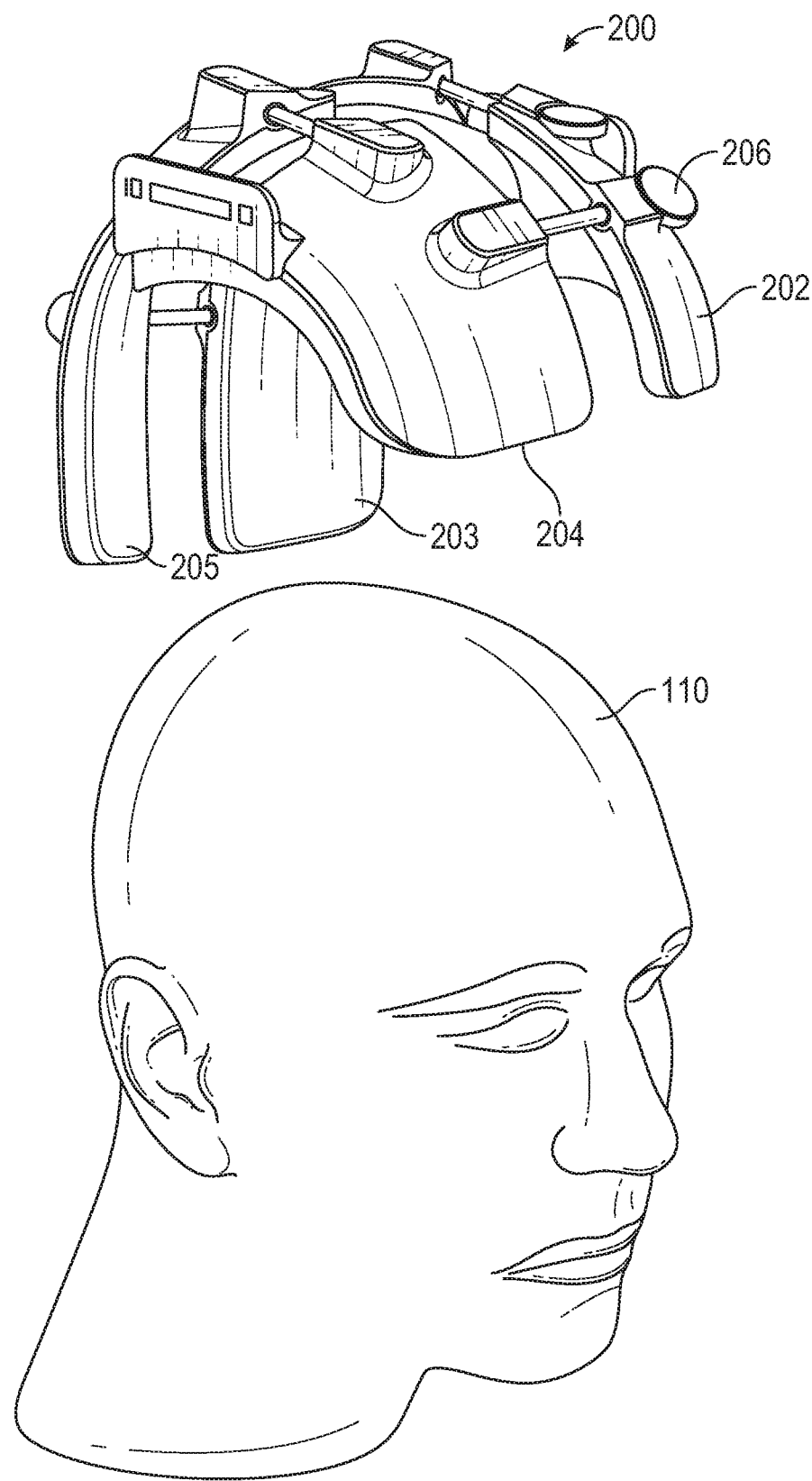
FIG. 7A illustrates a perspective view of a headset according to various embodiments.
Figure 7B:
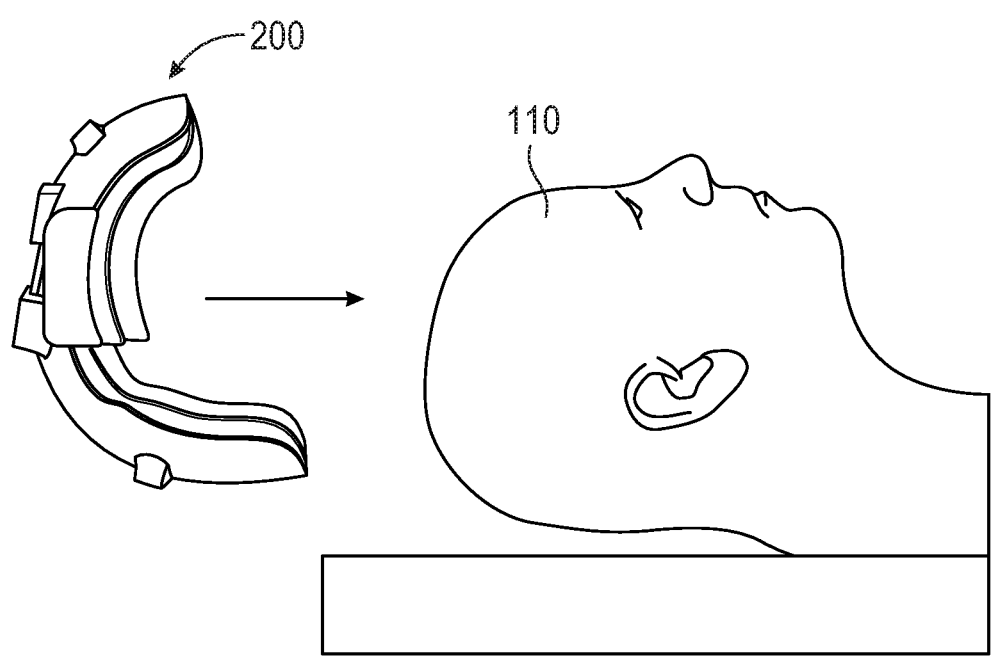
FIG. 7B illustrates a side view of the headset shown in FIG. 7A according to various embodiments.

FIG. 7A illustrates a perspective view of a headset 200 according to various arrangements. FIG. 7B illustrates a side view of the headset 200 shown in FIG. 7A according to various arrangements. Referring to FIG. 7A and FIG. 7B, in some arrangements, the headset 200 allows for use on a patient in a multitude of positions, ranging from sitting upright, as shown in FIG. 7A, to a horizontal position in which the patient is lying on his or her back, as shown in FIG. 7B, as well as a reclined position. In some arrangements, the headset 200 utilizes a four-quadrant clamping system that includes a first portion (front-left portion) 202, a second portion (rear-left portion) 203, a third portion (front-right portion) 204, and a fourth portion (rear-right portion) 205. In some arrangements, the first portion 202 is fastened to the third portion 204 using screws 206. In other arrangements, any suitable fastening mechanism is used, such as, but not limited to, clamps, Velcro straps, elastic bands, or any other suitable fastener. In some arrangements, the headset 200 is of a size and shape that is compatible with the human head 110 and can be slid onto the head 110, as shown in FIG. 7A, or slid under the head 110, as shown in FIG. 7B.

Figure 8:
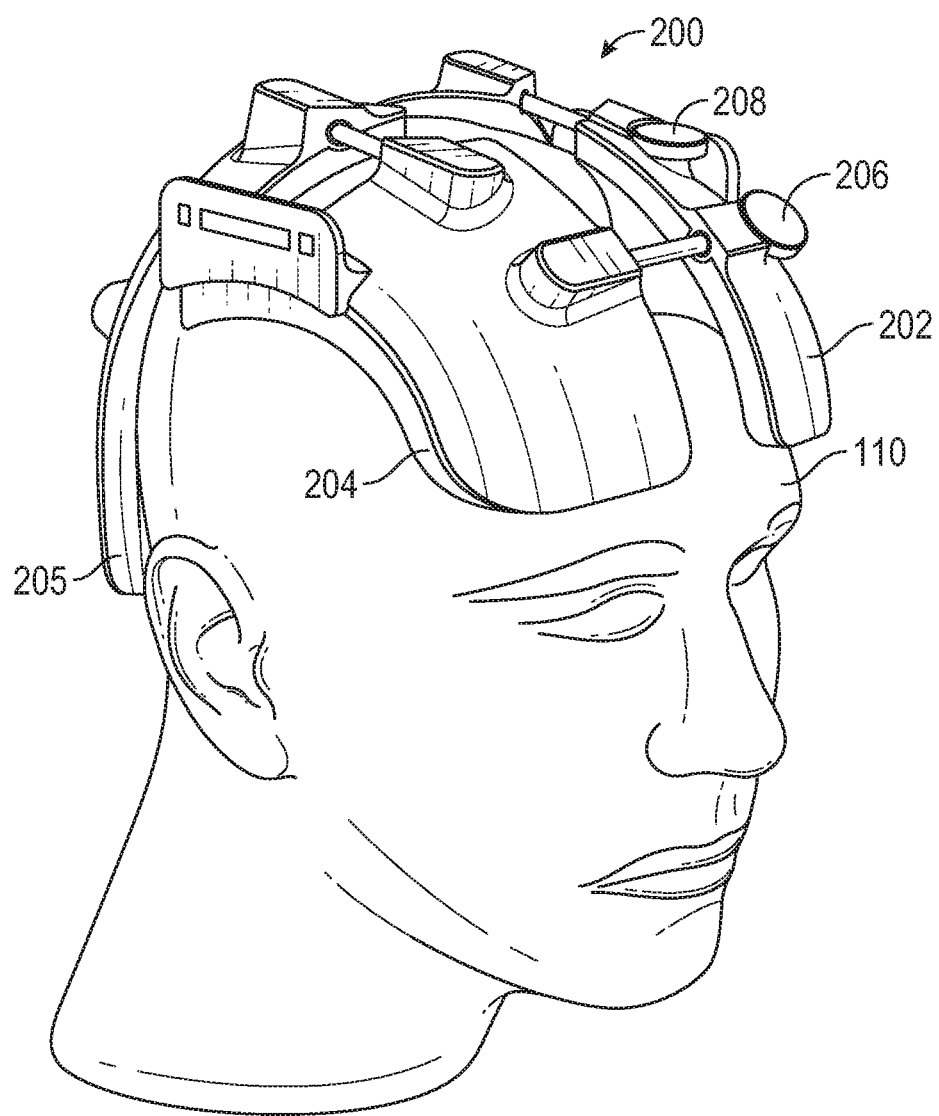
FIG. 8 illustrates a perspective view of a headset encasing a patient's head according to various embodiments.

FIG. 8 illustrates a perspective view of the headset 200 encasing the patient's head 110 according to various arrangements. Referring to FIG. 8, in some arrangements, the headset 200 is adjustable using the screw 206, or other suitable fastener, to fit the head 110 at the left and right sides of the head 110, as well as adjustable using a screw 208, or other suitable fastener, to fit the head 110 at the front and back sides of the head 110.

Figure 9:
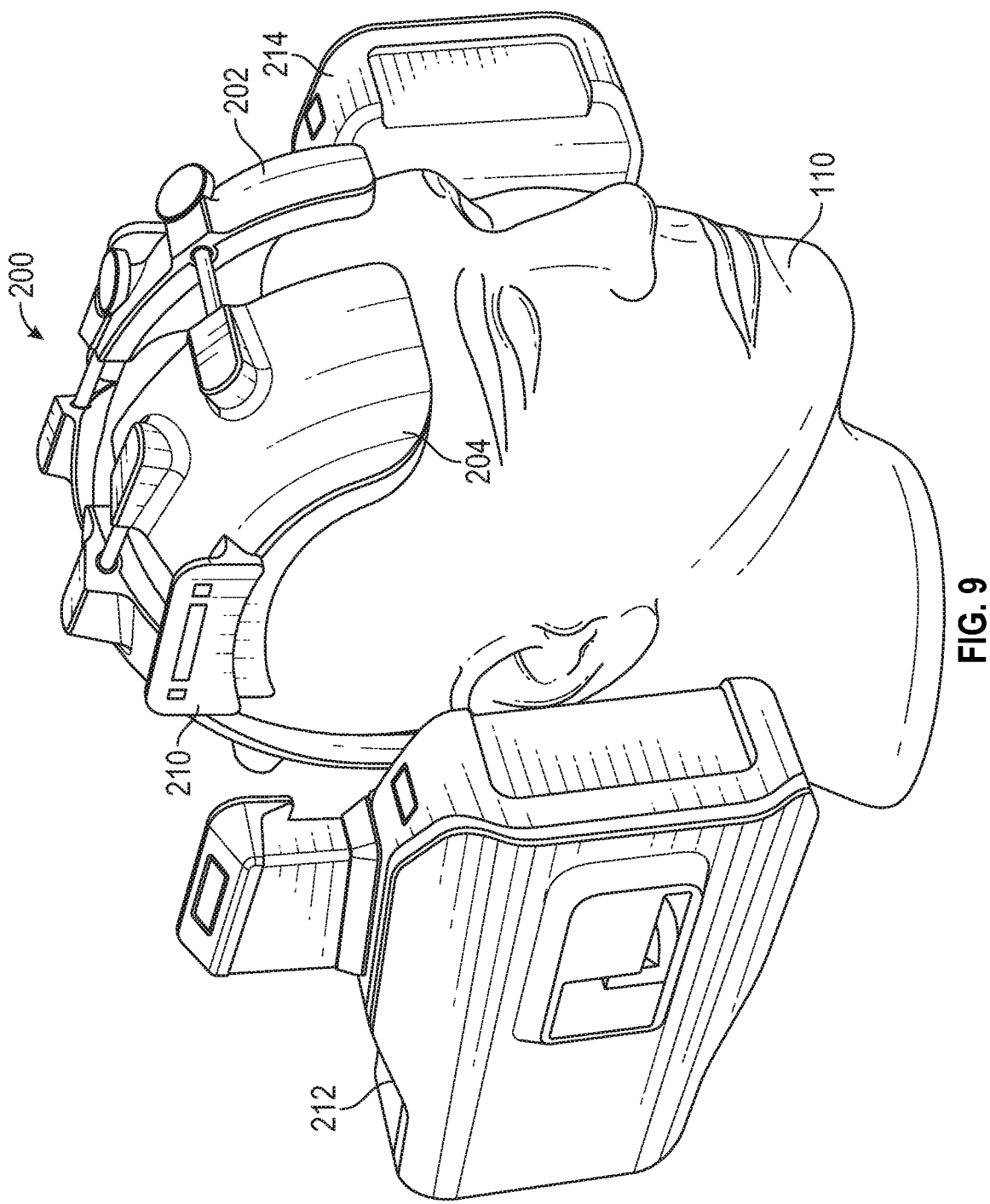
FIG. 9 illustrates a perspective view of a headset including robotic scanners encasing a patient's head according to various embodiments.

FIG. 9 illustrates a perspective view of the headset 200 including robotic pods or robotic scanners 212, 214 surrounding the patient's head 110 according to various arrangements. The description above relating to the robotic pods 174, 176 is applicable to the robotic scanners 212, 214. Referring to FIG. 9, in some arrangements, the headset 200 includes a connector 210 at the third portion 204 that allows the first robotic scanner 212 to attach to the headset 200. In some arrangements, the second robotic scanner 214 similarly connects to the headset 200 at the first portion 202. In some arrangements, the first robotic scanner 212 and the second robotic scanner 214 releasably connect to the headset 200, for example, by snap-fitting, latching, adhesive, by any other suitable method, and the like.

Figure 10:
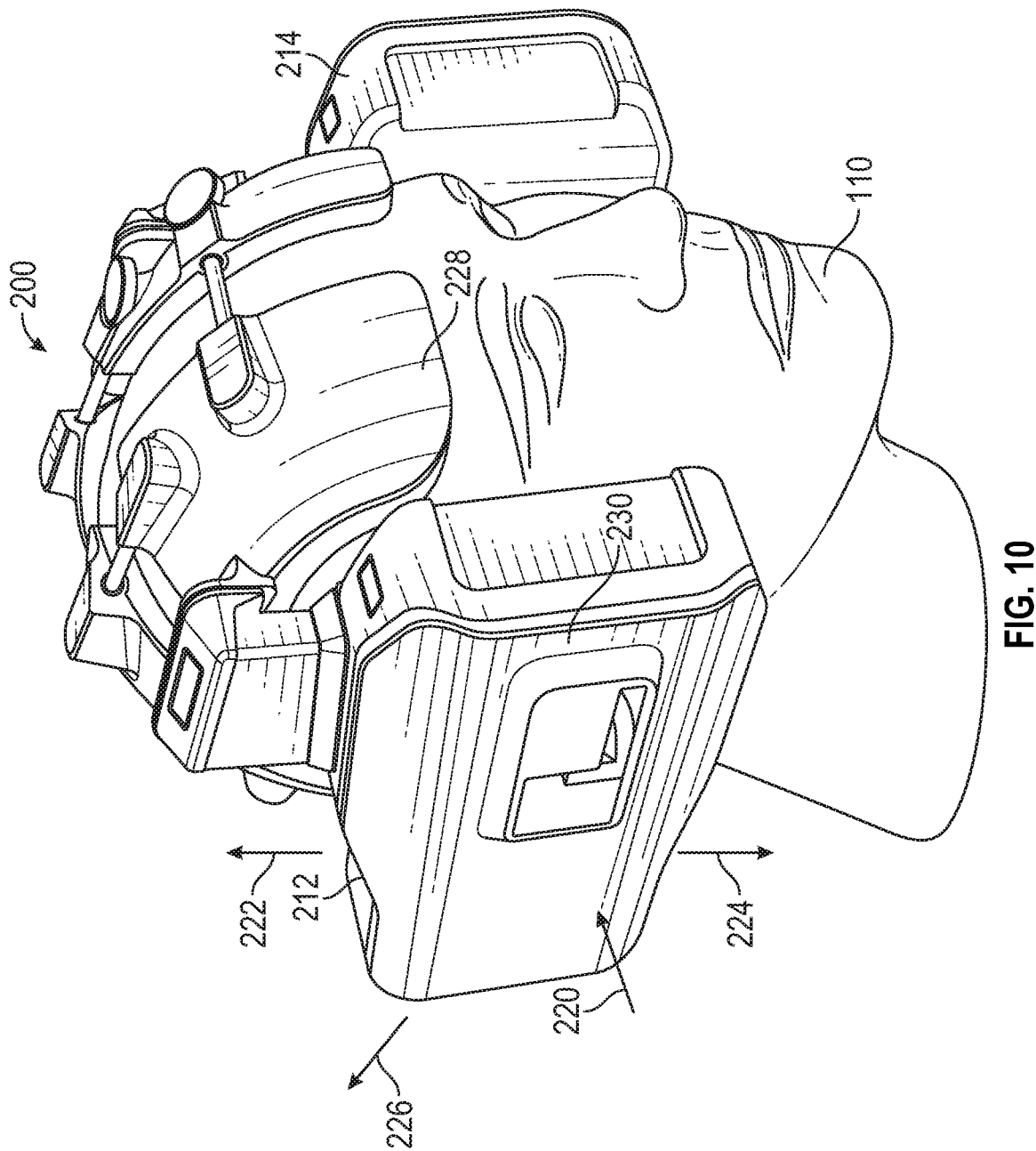
FIG. 10 illustrates a perspective view of a headset including adjustable robotic scanners encasing a patient's head according to various embodiments.

FIG. 10 illustrates a perspective view of the headset 200 including the adjustable robotic scanners 212, 214 surrounding the patient's head 110 according to various arrangements. Referring to FIG. 10, in some arrangements, the first robotic scanner 212 connected to the headset 200 is adjustable in an inward direction 220, in an upward direction 222, in a downward direction 224, in a backward direction 226, or in a forward direction, to adjust to different head shapes and locations of suitable acoustic windows at the patient head 110 that allow for suitable transmission of ultrasound energy into the brain of the patient from the robotic scanners 212, 214.

Figure 11:
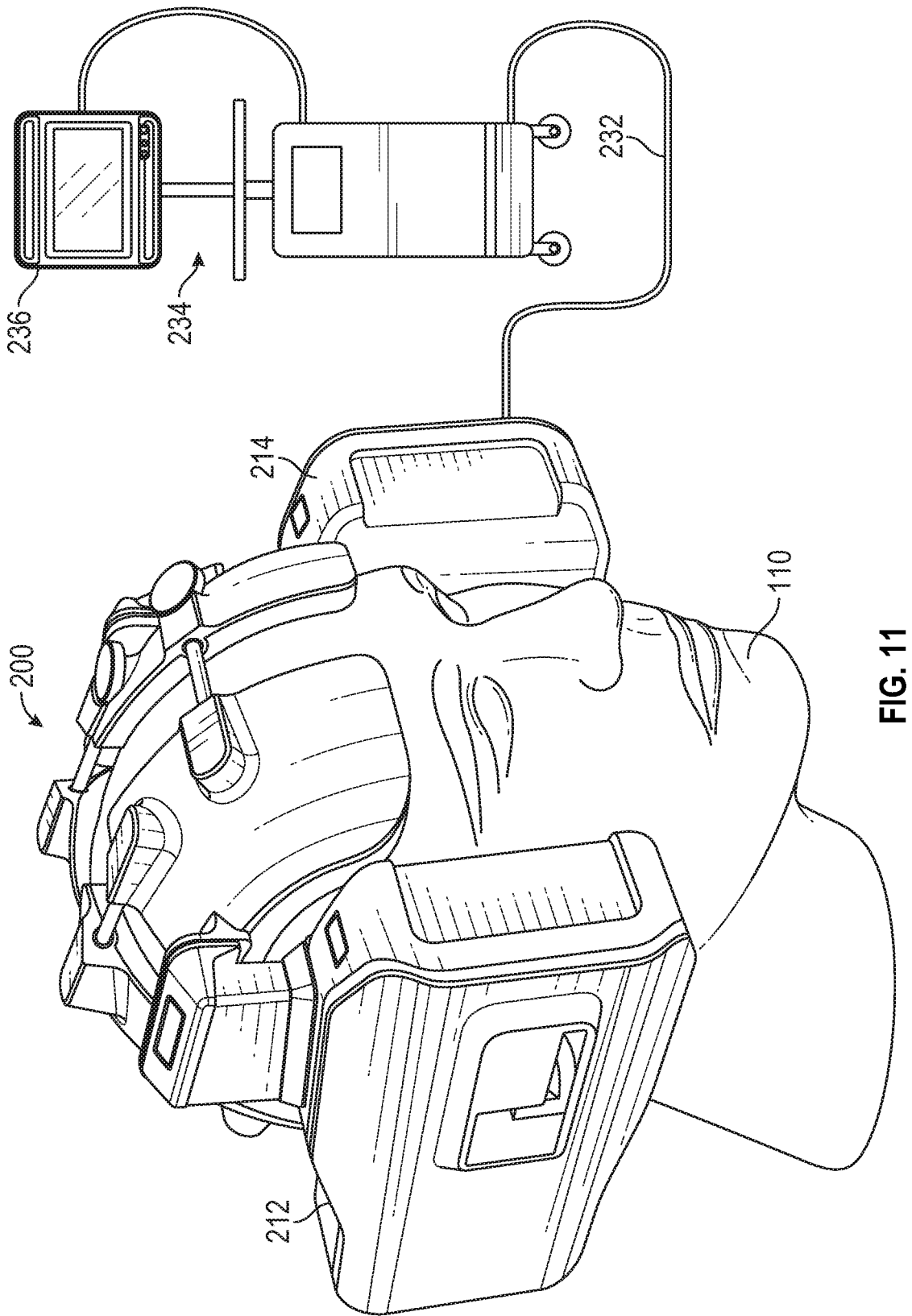
FIG. 11 illustrates a perspective view of a headset connected to a portable workstation according to various embodiments.

FIG. 11 illustrates a perspective view of the headset 200 connected to the portable workstation 234 according to various arrangements. Referring to FIG. 11, in some arrangements, the headset 200 includes the robotic scanners 212, 214 connected via a cable 232 to the portable workstation 234 including a monitor 236 to display results of the scanning of the patient. In some arrangements, the portable workstation 234 communicates with the robotic scanners 212, 214 using wireless communication technologies such as, but not limited to, Bluetooth, Wi-Fi, or any other suitable wireless communication technology.

Figure 12A:
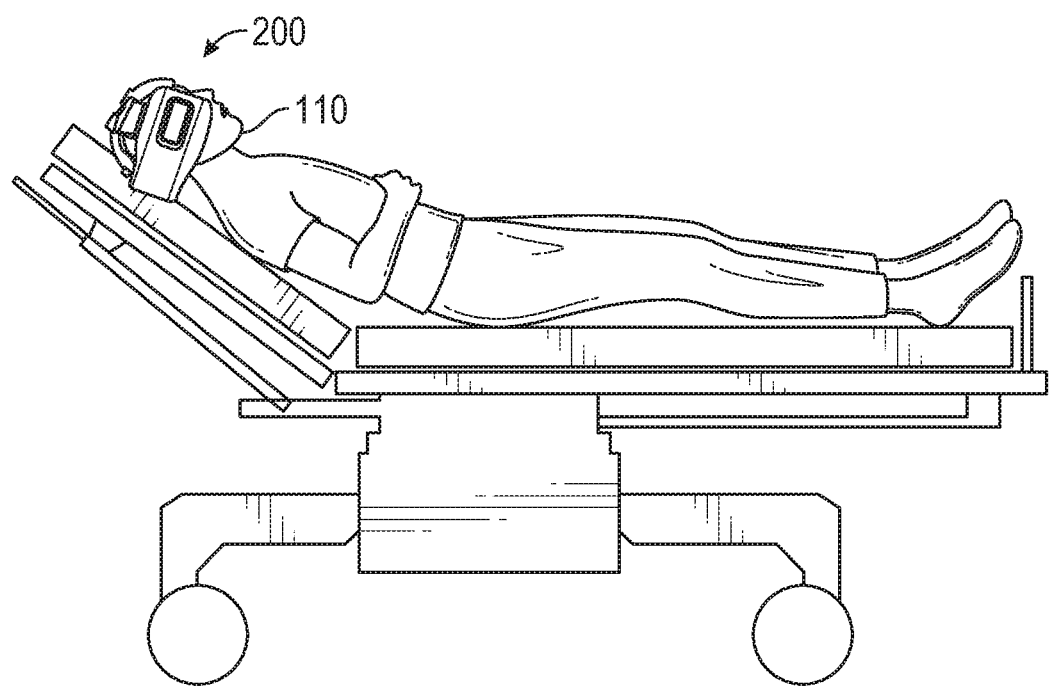
FIG. 12A illustrates an elevation view of a headset encasing a patient's head in a reclined position according to various embodiments.
Figure 12B:
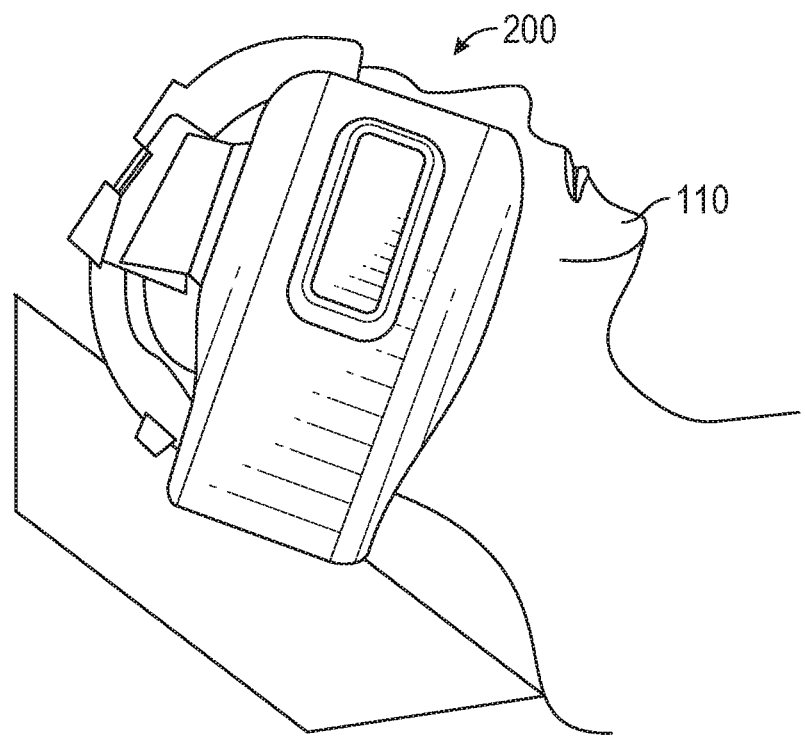
FIG. 12B illustrates an enlarged view of the headset encasing the patient's head in the reclined position as shown in FIG. 12A according to various embodiments.
Figure 12C:
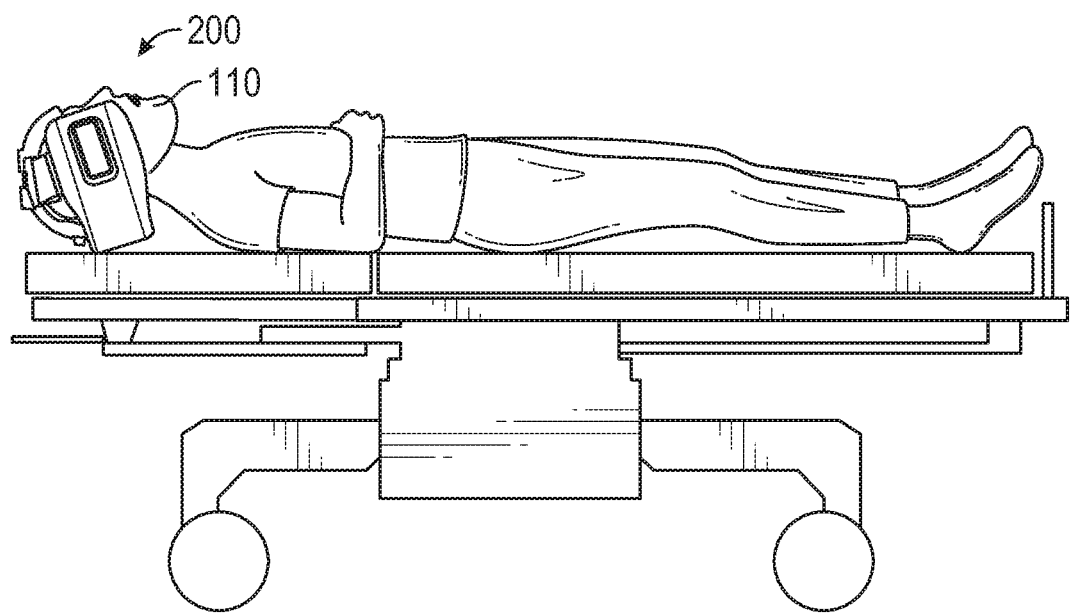
FIG. 12C illustrates an elevation view of a headset encasing a patient's head in a horizontal position according to various embodiments.
Figure 12D:
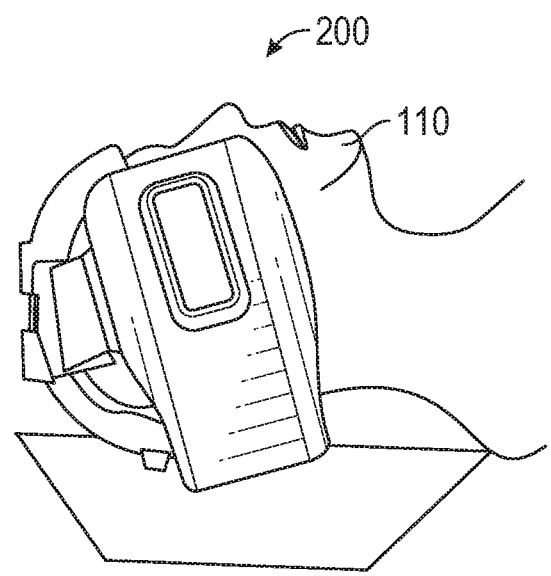
FIG. 12D illustrates an enlarged view of the headset encasing the patient's head in the horizontal position as shown in FIG. 12C according to various embodiments.

FIG. 12A illustrates an elevation view of the headset 200 encasing the patient's head 110 in a reclined position according to various arrangements. FIG. 12B illustrates an enlarged view of the headset 200 encasing the patient's head 110 in the reclined position as shown in FIG. 12A according to various arrangements. FIG. 12C illustrates an elevation view of the headset 200 encasing the patient's head 110 in a horizontal position according to various arrangements. FIG. 12D illustrates an enlarged view of the headset 200 encasing the patient's head 110 in the horizontal position as shown in FIG. 12C according to various arrangements. Referring to FIG. 12A, in some arrangements, the headset 200 can be placed on the head 110 of the patient that is in a reclined position, as shown in further detail in FIG. 12B. Referring to FIG. 12C, in some arrangements, the headset 200 can be placed on the head 110 of the patient that is in a horizontal position, as shown in further detail in FIG. 12D.

In some arrangements, the headset 200 includes the plurality of head pieces 202, 203, 204, 205 and the one or more robotic pods 212, 214. In some arrangements, the robotic pods 212, 214 are similar to the robotic pod 174 described above, and in other arrangements, include manual probe adjustment mechanisms. In some arrangements, the head pieces 202, 203, 204, 205 are configured to contact and be contoured to align with the shape of the head 110 of the subject. In some arrangements, the head pieces 202, 203, 204, 205 are configured to be positioned at the four quadrants (or corners) of the head 110. In some arrangements, the head pieces 202, 203, 204, 205 include padding therein to contact the head 110, as described herein.

In some arrangements, connectors located between the head pieces 202, 203, 204, 205 provide an inward force between the head pieces 202, 203, 204, 205 such that the head pieces 202, 203, 204, 205 are drawn into one another. For example, the connectors can include springs therein to exert the inward force between the head pieces 202, 203, 204, 205 (e.g., a spring tension force), and the springs can be calibrated to adjust the amount of spring force. In some arrangements, the head pieces 202, 203, 204, 205 are manually pulled apart from one another such that the inward force provided by the connectors allow the head pieces 202, 203, 204, 205 to be held fast against the head 110 when the headset 200 is worn. In other arrangements, any suitable number of head pieces 202, 203, 204, 205 and connectors therebetween can be used to provide a stable headset.

Figure 13:
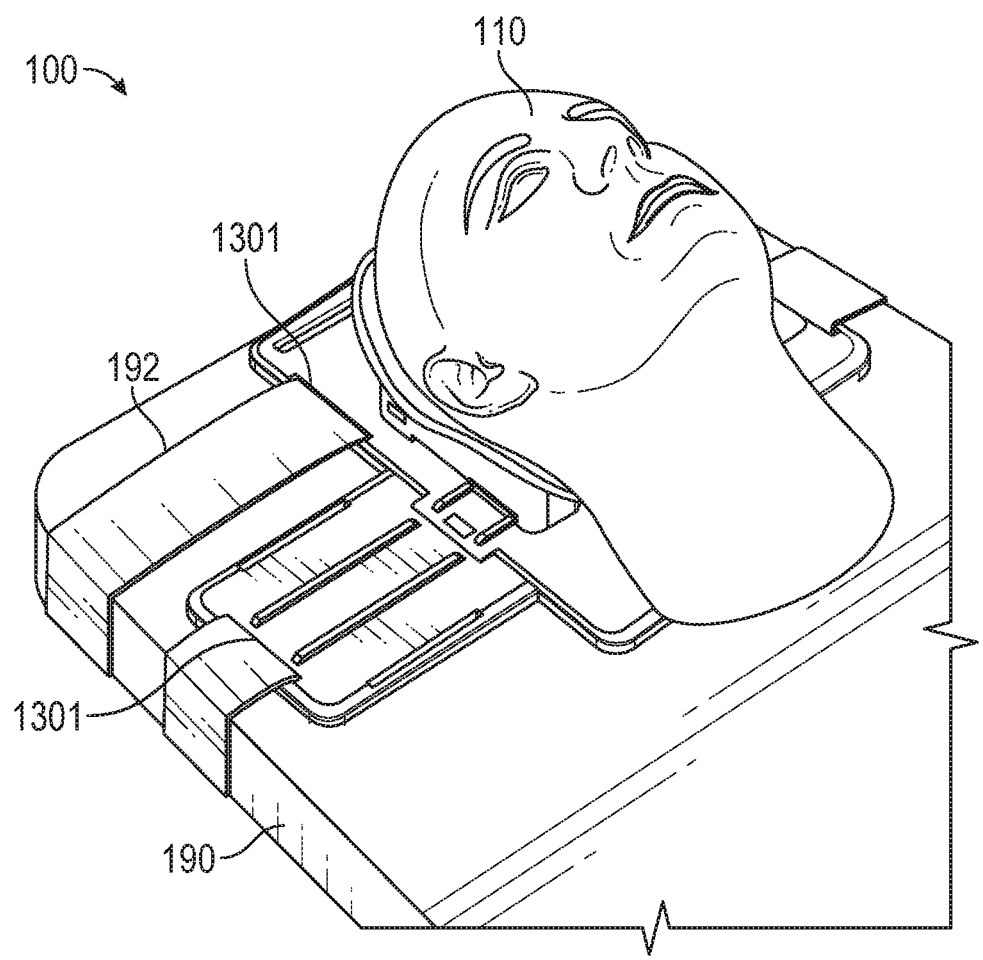
FIG. 13 illustrates a perspective view of a headset including a plurality of straps according to various embodiments.

FIG. 13 illustrates a perspective view of the supine headset 100 including a plurality of straps 192 according to various arrangements.

In some arrangements, the supine headset 100 includes a plurality of anchor points 1301 at edges of the supine headset 100. In some arrangements, the straps 192 are secured (e.g., tied) to the anchor points 1301 of the supine headset 100 and tied to the surface on which the supine headset 100 rests (e.g., a gurney or a bed). The surface may be flat or substantially flat. Accordingly, the supine headset 100 is securely fastened and stable with respect to the surface upon which the supine headset 100 rests. In other arrangements, the supine headset 100 is secured to the surface in any other suitable manner, such as, but not limited to, adhesive, bolting, welding, and the like. In some arrangements, the anchor points 1301 are slots through which the straps 192 are tied. In some arrangements, the straps 192 are made from any suitable strong material, such as, but not limited to, metal, nylon, leather, and the like. In other arrangements, the supine headset 100 includes only one strap 192 for securing the supine headset 100 to the surface. In yet other arrangements, the supine headset 100 includes three or more straps 192 for securing to a surface.

Figure 14:
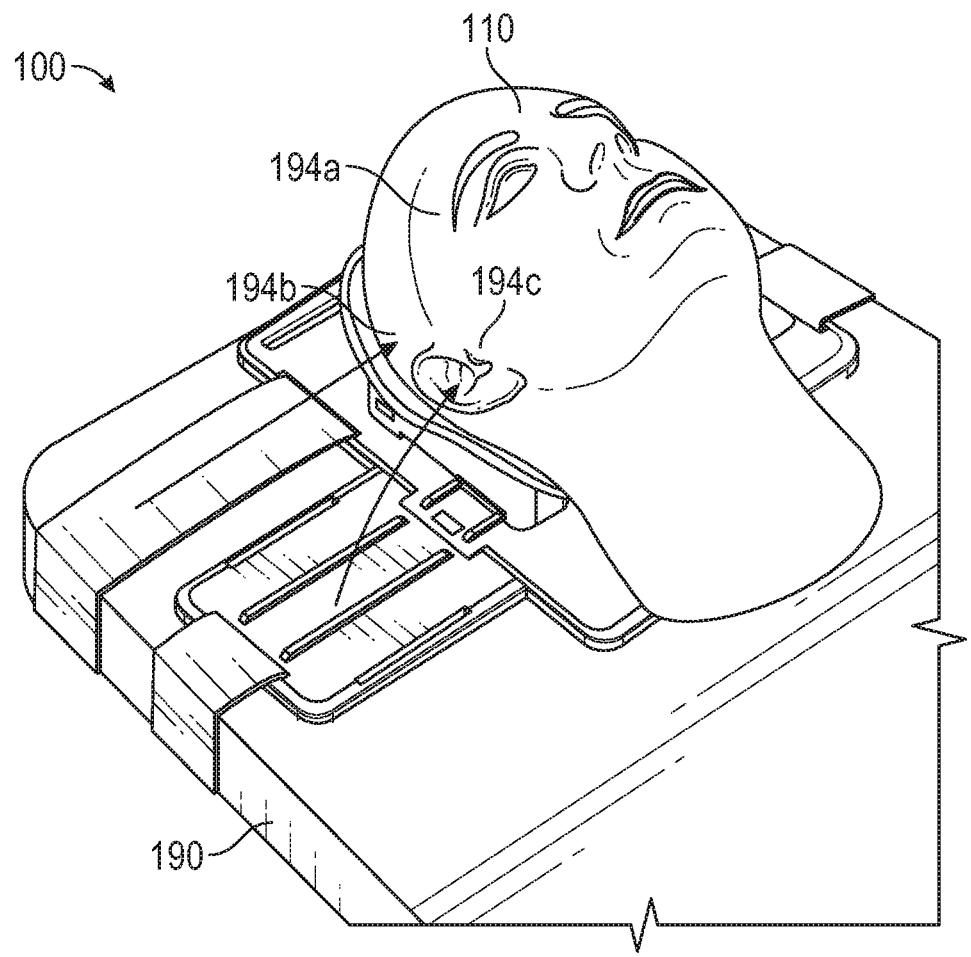
FIG. 14 illustrates a perspective view of a headset according to various embodiments.

FIG. 14 illustrates a perspective view of the supine headset 100 according to various arrangements.

In some arrangements, an operator of the supine headset 100 can place fiducial markers 194a, 194b, 194c on the head 110. In some arrangements, the fiducial markers 194a, 194b, 194c are disposed at anatomically significant locations such that an image taken by the robotic pods 174, 176 includes the subject's head with the fiducial markers 194a, 194b, 194c. In some arrangements, the fiducial markers 194a, 194b, 194c are disposed at anatomically significant locations so as to signify the boundaries of the workspace of the robotic pods 174, 176 during operation, and the fiducial markers 194a, 194b, 194c are configured to be detected by an image processing circuit of the robotic pods 174, 176. In particular arrangements, the fiducial markers 194a, 194b, 194c are disposed at a corner of a subject's eye and at the tragus of the subject. In some arrangements, any suitable number of fiducial markers can be disposed on a subject, such as, but not limited to, one fiducial, two fiducials, or three or more fiducial markers. In some arrangements, the fiducial markers 194a, 194b, 194c are adhesive stickers having a fixed size, shape, and design, and include a circular retroreflective material and a surrounding black ring.

Figure 15:
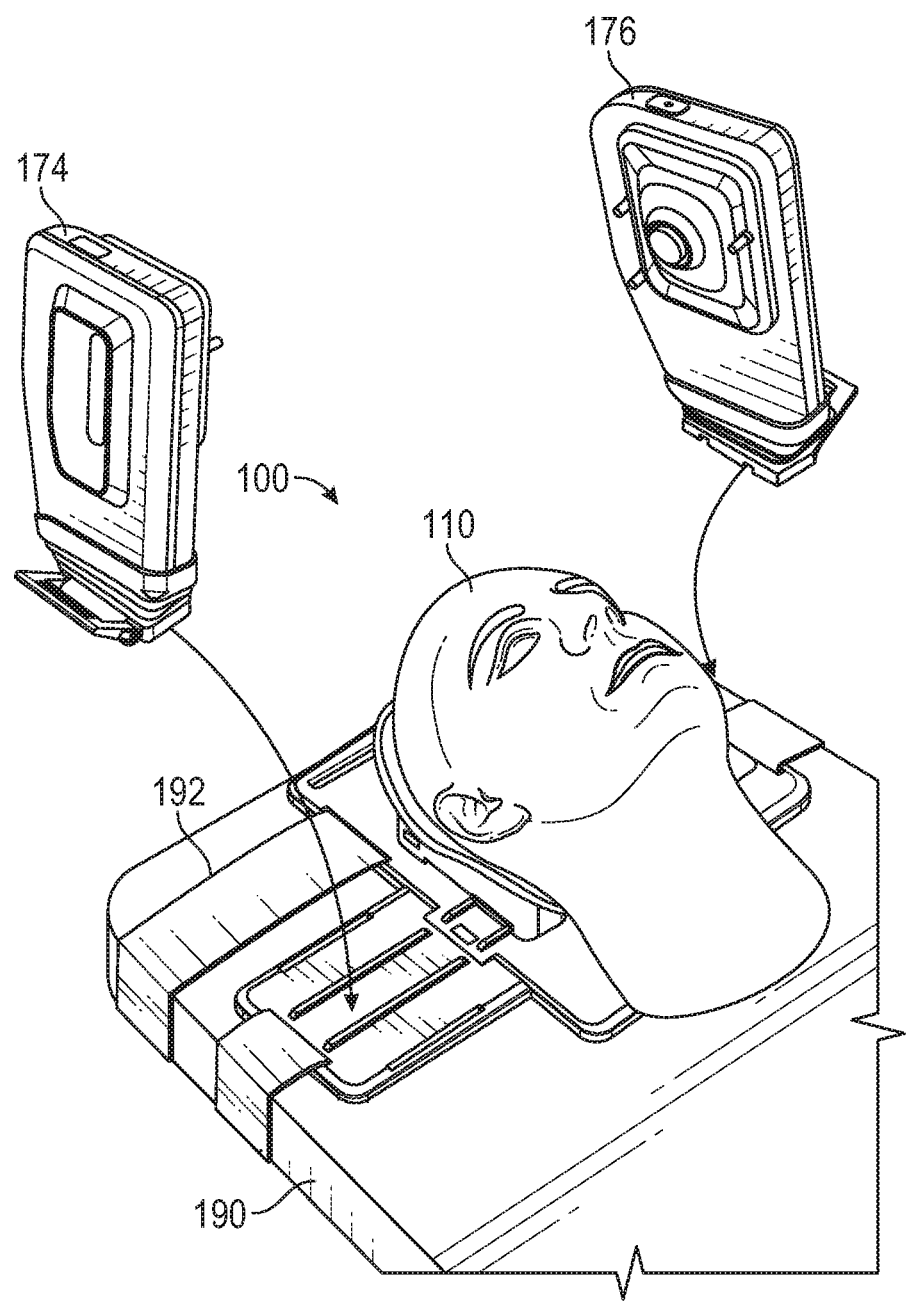
FIG. 15 illustrates a perspective view of a headset including robotic pods according to various embodiments.

FIG. 15 illustrates a perspective view of the supine headset 100 including the robotic pods 174, 176 according to various arrangements. In some arrangements, the robotic pods 174, 176 are affixed to the baseplate 120 as described above.

Figure 16:
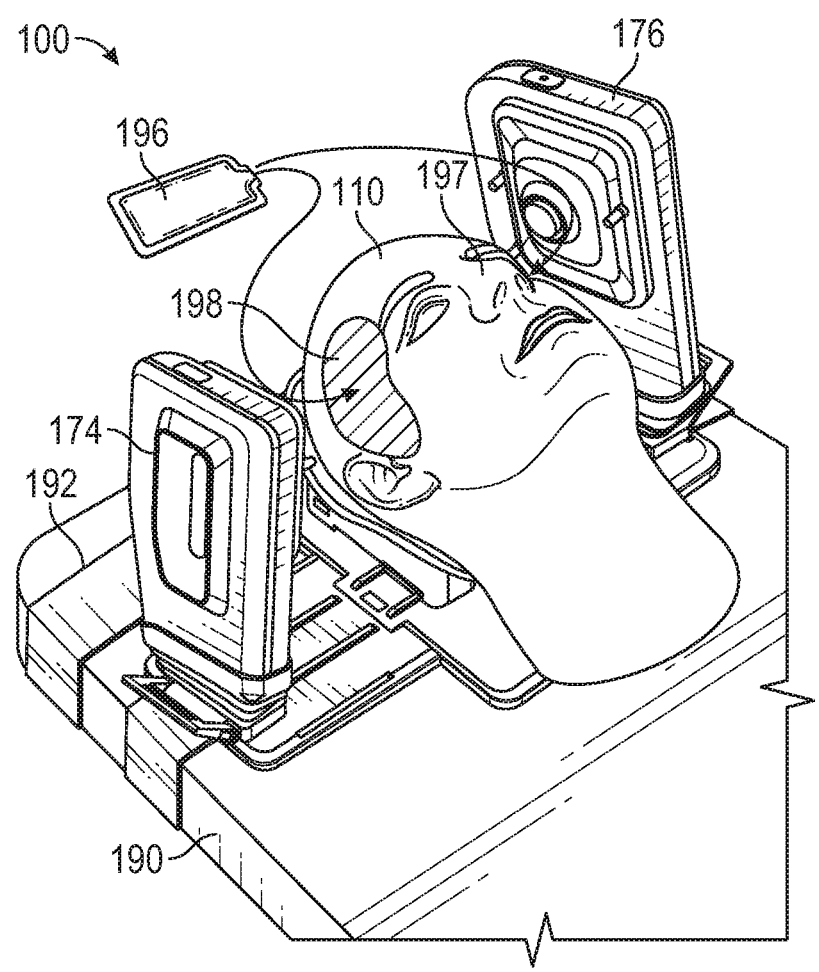
FIG. 16 illustrates a perspective view of a headset including robotic pods according to various embodiments.

FIG. 16 illustrates a perspective view of the supine headset 100 including the robotic pods 174, 176 according to various arrangements. In some arrangements, gel 196 is disposed at acoustic windows of the head 110 for use with the probes of the robotic pods 174, 176. Each of the probes of the robotic pods 174, 176 is configured to contact or be proximate an acoustic window (e.g., temporal window) of the head 110. In other words, the probe of the robotic pod 174 can be positioned to contact or be proximate a right temporal window of the head 110. The probe of the robotic pod 176 can be positioned to contact or be proximate a left temporal window of the head 110.

In some arrangements, use of the supine headset 100 begins by the portable workstation 178 being moved to the patient location. The portable workstation 178 is moved close to the head 110 of the patient. The portable workstation 178 is turned on, electrical connections are checked, and normal operation of the monitor 180 is checked. The supine headset 100 is removed from the portable workstation 178 and unfolded for operation with respect to the patient's head.

In some arrangements, the head 110 of the patient is gently lifted and the supine headset 100 is slid into position underneath the head 110. The left-side restraint 130 and the right-side restraint 140 are adjusted to cradle the head 110 therebetween. In some arrangements, the supine headset 100 is secured to the bed or gurney 190, on which the patient is located, using the straps 192 or other suitable fastener.

In some arrangements, the registration stickers or fiducial markers 194a, 194b, 194c are placed on the head 110 of the patient. Fiducial markers 194a, 194b, 194c are placed on the head 110 at anatomical features of interest by an operator. There are several identical fiducial markers, or markers or fiducials, which are distinguishable from one another, and they may have a known pattern that allows for determination of their orientation by image processing or be simplified marks without any such pattern. In some arrangements, fiducial markers 194a, 194b, 194c include stickers to be affixed to the skin or simple dots drawn on the skin (e.g., with a biocompatible semi-permanent marker). In some arrangements, the fiducial markers 194a, 194b, 194c are of a known size so that image processing techniques can be used to determine the distance of the fiducial markers 194a, 194b, 194c in the captured image. In some arrangements, the fiducial markers 194a, 194b, 194c are made from a reflective material, combined with an illumination source outside the visible spectrum and a camera filtering out light sources other than that illumination source, to improve the system robustness in various light conditions which avoids issues that may result from poor lighting, glare, etc.

In some arrangements, the first robotic pod 174 and the second robotic pod 176 are unpacked, connected to the portable workstation 178, and their connections are checked. In some arrangements, the first robotic pod 174 and the second robotic pod 176 are mounted to the baseplate 120 of the supine headset 100. In some arrangements, ultrasound gel 196 is applied to the first side 197 and the second side 198 of the head 110 of the patient, and more specifically, for example, to the temporal window of the head 110 where ultrasound probes of the pods 174, 176 are configured to contact. Then, general registration of the first robotic pod 174 and the second robotic pod 176 is performed to locate an appropriate ultrasound energy window or temporal window. In some arrangements, fine registration of the first robotic pod 174 and the second robotic pod 176 is performed automatically. In other words, the robotics described herein can automatically control the position of the ultrasound probes of the pods 174, 176 against the temporal window of the head 110 of the subject. As such, a scan of the head 110 of the patient is performed.

In some arrangements, use of the headset 200 begins by the portable workstation 234 being moved generally to the patient location. The portable workstation 234 is moved close to the head 110 of the patient. The portable workstation 234 is turned on, electrical connections are checked, and normal operation of the monitor 236 is checked. In some arrangements, the headset 200 is removed from the portable workstation 234 and expanded for placement onto the head 110.

In some arrangements, the patient is gently lifted and the headset 100 is slid into position on the head 110. In some arrangements, the supine headset 200 is adjusted using the screw 206 and the screw 208 to properly fit the headset 200 onto the head 110. In some arrangements, the first robotic scanner 212 and the second robotic scanner 214 are unpacked, connected to the portable workstation 234, and their connections are checked.

In some arrangements, the fiducial markers 194a, 194b, 194c are placed onto the head 110 of the patient. The fiducial markers 194a, 194b, 194c may be placed on the head 110 at anatomical features of interest by an operator. In some arrangements, ultrasound gel 196 is applied to the first side 197 and the second side 198 of the head 110 of the patient, and more specifically, for example, to the temporal window of the head 110 where ultrasound probes of the pods 174, 176 are configured to contact. In some arrangements, the first robotic scanner 212 and the second robotic scanner 214 are mounted to the headset 200. In some arrangements, general registration of the first robotic scanner 212 and the second robotic scanner 214 is performed to locate an appropriate ultrasound energy window or temporal window. In some arrangements, fine registration of the first robotic scanner 212 and the second robotic scanner 214 is performed automatically. In other words, the robotics described herein can automatically control the position of the ultrasound probes of the scanner 212, 214 against the temporal window of the head 110 of the subject.

In other arrangements, the headsets described herein are positioned such that a subject is in a seated position, and the subject's head is vertical. In particular arrangements, the headset is mounted to a vertical platform such that the subject's head bears little or no weight of the headset. For example, the vertical headset can be mounted to a wall, a chair, and the like.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

What is claimed is:

1. An ultrasound device comprising:
    a baseplate;
    a transducer configured to transmit or receive ultrasound energy with respect to a head of a subject;
    robotics coupled to the transducer and configured to control a position of the transducer relative to the head of the subject when the ultrasound device is attached to a headset; and
    a housing that encloses at least a portion of the transducer and at least a portion of the robotics, wherein the housing comprising the transducer and the robotics is configured to be removably attached to the headset by inserting in a direction toward the baseplate to be placed at a specific position relative to the head of the subject when the head of the subject is supported by the baseplate.

2. The ultrasound device of claim 1, wherein the ultrasound device is configured to be removably attached to be in the position that is adjacent a side of the head of the subject.

3. The ultrasound device of claim 1, wherein the baseplate comprises a railway and the ultrasound device is configured to be removably attached to the railway.

4. The ultrasound device of claim 3, wherein the position of the ultrasound device is adjustable along the railway.

5. The ultrasound device of claim 4, wherein the position of the ultrasound device is configured to be adjusted by adjusting a distance of the ultrasound device from the side of the head of the subject.

6. The ultrasound device of claim 4, wherein an entirety of the ultrasound device is configured to move as the position of the ultrasound device is adjusted along the railway.

7. The ultrasound device of claim 1, further comprising a latch, wherein the ultrasound device is attached to or removed from the baseplate in response to actuation of the latch.

8. The ultrasound device of claim 1, wherein the transducer is configured to be located proximate to or in contact with a temporal window of the head of the subject.

9. The ultrasound device of claim 1, wherein a position of the housing in relation to the headset is configured to be adjustable.

10. The ultrasound device of claim 1, wherein a position of the robotics in relation to the headset is configured to be adjustable.

11. A method of manufacturing an ultrasound device, the method comprising:
    providing a baseplate;
    providing a transducer configured to transmit or receive ultrasound energy with respect to a head of a subject; and
    providing a housing that encloses at least a portion of the transducer and at least a portion of the robotics;
    configuring the housing the housing comprising the transducer and the robotics to be removably attached to the headset by inserting in a direction toward the baseplate to be placed at a specific position relative to the head of the subject when the head of the subject is supported by the baseplate.

12. The method of claim 11, wherein the baseplate is configured to receive the head of the subject; and the ultrasound device is configured to be removably attached to be in the position that is adjacent a side of the head of the subject.

13. The method of claim 11, wherein the baseplate comprises a railway and the ultrasound device is configured to be removably attached to the railway.

14. The method of claim 13, wherein the position of the ultrasound device is adjustable along the railway.

15. The method of claim 14, wherein the position of the ultrasound device is configured to be adjusted by adjusting a distance of the ultrasound device from the side of the head of the subject.

16. The method of claim 14, wherein an entirety of the ultrasound device is configured to move as the position of the ultrasound device is adjusted along the railway.

17. The method of claim 11, further comprising installing a latch to the ultrasound device, wherein the ultrasound device is attached to or removed from the baseplate in response to actuation of the latch.

* * * * *